US011460444B2

(12) United States Patent
Mlcak et al.

(10) Patent No.: US 11,460,444 B2
(45) Date of Patent: *Oct. 4, 2022

(54) AIRCRAFT AIR CONTAMINANT ANALYZER AND METHOD OF USE

(71) Applicant: Pall Corporation, Port Washington, NY (US)

(72) Inventors: Richard Mlcak, Bolton, MA (US); Patrick Gwynne, Stow, MA (US); Aidan Kodas, Waltham, MA (US); Justin Abramson, Brookline, MA (US)

(73) Assignee: Pall Corporation, Port Washington, NY (US)

( * ) Notice: Subject to any disclaimer, the term of this patent is extended or adjusted under 35 U.S.C. 154(b) by 834 days.

This patent is subject to a terminal disclaimer.

(21) Appl. No.: 16/392,219

(22) Filed: Apr. 23, 2019

(65) Prior Publication Data

US 2020/0340950 A1 Oct. 29, 2020

(51) Int. Cl.
*G01N 29/036* (2006.01)
*G01N 29/22* (2006.01)
(Continued)

(52) U.S. Cl.
CPC ......... *G01N 29/036* (2013.01); *G01N 29/222* (2013.01); *G01N 29/4454* (2013.01);
(Continued)

(58) Field of Classification Search
CPC ............ G01N 29/036; G01N 29/222; G01N 29/4454; G01N 29/4427; G01N 29/022;
(Continued)

(56) References Cited

U.S. PATENT DOCUMENTS 5,356,594 A 10/1994 Neel et al.
6,128,561 A 10/2000 Janata
(Continued)

FOREIGN PATENT DOCUMENTS

EP 0675267 A1 10/1995
EP 2593767 A2 5/2013
(Continued)

OTHER PUBLICATIONS

Voiculescu et al., "Micropreconcentrator for Enhanced Trace Detection of Explosives and Chemical Agents," *IEEE Sensors Journal*, 6(5): 1094-1104 (2006).
(Continued)

*Primary Examiner* — Suman K Nath
(74) *Attorney, Agent, or Firm* — Leydig, Voit & Mayer, Ltd.

(57) ABSTRACT

A method and an aircraft air contaminant analyzer for determining and classifying air contaminants, providing a sample flow path and bypass flow path bypassing the sample flow path, are disclosed, the analyzer comprising a contaminant collector comprising a medium desorbing captured contaminants, the collector providing a first sample flow path; a heater vaporizing captured contaminants; a bypass comprising a channel including a second sample flow path, the channel bypassing the collector; a sensor responding when air contaminant mass is added to or removed from the sensor, for classifying contaminant type; the sensor receiving contaminants desorbed from the medium; a frequency measurement device measuring the response generated by the sensor as the air contaminant is added to and removed from the sensor; a computer readable medium bearing a contaminant recognition program and calibration data; and, a processor executing the program, the program including a module classifying the contaminant by type.

26 Claims, 14 Drawing Sheets

(51) Int. Cl.
*G01N 29/44* (2006.01)
*G01N 33/00* (2006.01)

(52) U.S. Cl.
CPC ..... *G01N 33/0016* (2013.01); *G01N 33/0062* (2013.01); *G01N 2291/014* (2013.01); *G01N 2291/0215* (2013.01); *G01N 2291/02809* (2013.01)

(58) Field of Classification Search
CPC .......... G01N 33/0016; G01N 33/0062; G01N 33/0047; G01N 2291/014; G01N 2291/0215; G01N 2291/02809; G01N 2291/02408; G01N 2291/02425; G01N 2291/0256; G01N 2291/0427; G01N 1/4022; G01N 1/2214; G01N 1/2247; G01N 5/00; G01N 15/0606; G01N 2015/0046; B64D 13/06; B64F 5/60
See application file for complete search history.

(56) References Cited

U.S. PATENT DOCUMENTS

| | | | |
|---|---|---|---|
| 6,171,378 | B1 | 1/2001 | Manginell et al. |
| 6,212,938 | B1 | 4/2001 | Staples |
| 6,289,287 | B1 | 9/2001 | Meng et al. |
| 6,354,160 | B1 | 3/2002 | Staples et al. |
| 6,421,588 | B1 | 7/2002 | Janata |
| 6,627,965 | B1 | 9/2003 | Tuller et al. |
| 6,711,470 | B1 | 3/2004 | Hartenstein et al. |
| 6,839,636 | B1 | 1/2005 | Sunshine et al. |
| 6,953,977 | B2 | 10/2005 | Mlcak et al. |
| 7,103,481 | B2 | 9/2006 | Negri |
| 7,547,931 | B2 | 6/2009 | Star et al. |
| 7,917,309 | B2 | 3/2011 | Brodsky |
| 7,955,574 | B2 | 6/2011 | Fryxell et al. |
| 8,221,828 | B2 | 7/2012 | Chinn et al. |
| 8,366,630 | B2 | 2/2013 | Haick et al. |
| 8,652,853 | B2 | 2/2014 | Markowitz et al. |
| 9,296,839 | B2 | 3/2016 | Venema et al. |
| 9,459,223 | B1 | 10/2016 | Alqahtani et al. |
| 9,599,564 | B1 | 3/2017 | Li |
| 2004/0060344 | A1 | 4/2004 | Kauffman et al. |
| 2005/0016276 | A1 | 1/2005 | Guan et al. |
| 2005/0160792 | A1 | 7/2005 | Booker |
| 2007/0086921 | A1 | 4/2007 | Visel et al. |
| 2009/0141769 | A1 | 6/2009 | Baldwin et al. |
| 2010/0130796 | A1 | 5/2010 | Combes et al. |
| 2013/0199271 | A1 | 8/2013 | Beer et al. |
| 2016/0258918 | A1 | 9/2016 | Groves |
| 2016/0327518 | A1 | 11/2016 | Matheron et al. |
| 2016/0364852 | A1 | 12/2016 | Omodt et al. |
| 2017/0045399 | A1 | 2/2017 | Lash et al. |
| 2017/0097255 | A1 | 4/2017 | Karakaya |
| 2017/0115197 | A1 | 4/2017 | Niemelä et al. |
| 2017/0248571 | A1* | 8/2017 | Perreault ............... F01D 25/183 |
| 2017/0342276 | A1 | 11/2017 | Wang et al. |
| 2017/0363524 | A1 | 12/2017 | Reed |
| 2018/0118351 | A1* | 5/2018 | Fox ........................ B64D 13/00 |
| 2018/0148180 | A1 | 5/2018 | Fagundes et al. |
| 2020/0340889 | A1 | 10/2020 | Mlcak et al. |
| 2020/0340890 | A1 | 10/2020 | Mlcak |
| 2020/0340949 | A1 | 10/2020 | Mlcak et al. |

FOREIGN PATENT DOCUMENTS

| | | |
|---|---|---|
| GB | 2506991 A | 4/2014 |
| JP | 2001-242057 A | 9/2001 |
| JP | 2007-248323 A | 9/2007 |
| JP | 2017-517729 A | 6/2017 |
| JP | 2019-2912 A | 1/2019 |
| WO | WO 2004/005907 A1 | 1/2004 |
| WO | WO 2013/064157 A1 | 5/2013 |
| WO | WO 2016/189420 A1 | 12/2016 |
| WO | WO 2018/089674 A1 | 5/2018 |

OTHER PUBLICATIONS

Intellectual Property Office of Singapore; Search Report in counterpart Singapore Patent Application No. 10202002679V, dated Feb. 5, 2021.

Bao Yuyang et al: "Resonant-gravimetric particle sensors with air-filtering cantilever fabricated in low-cost non-SOI silicon", 2018 *Micro Electro Mechanical Systems* (MEMS), IEEE, Jan. 21, 2018, pp. 908-911, XP033335731, DOI: 10.1109/MEMSYS.2018. 8346704.

European Patent Office; extended European Search Report including the European Search Report and the European Search Opinion in counterpart European Patent Application No. 20 164 522.3, dated Sep. 4, 2020.

Pall Corporation, "Gaskleen® Pico1000 Analyzer," Product Data Sheet (Aug. 2015).

Wikipedia, "Triethoxysilane," (Jul. 7, 2015) accessed at <en.wikipedia. org/wiki/Triethoxysilane> on Jan. 11, 2019.

European Patent Office, Extended European Search Report in European Patent Application No. 20164520.7, dated Sep. 25, 2020.

* cited by examiner

AIRCRAFT AIR CONTAMINANT ANALYZER AND METHOD OF USE

BACKGROUND OF THE INVENTION

Contaminants such as turbine engine oil and hydraulic fluid can be present in air or other gasses in the cabin/cockpit of an aircraft, during flight and/or during ground operation. Certain contaminants can be present in aerosol form, particulate form, and/or gaseous form, and the quantity of contaminants can vary significantly, even over orders of magnitude, leading to sensor fouling and/or delayed sensor response. When a plurality of contaminants are present, they may differ in quantity, such that certain contaminants (present in higher or lower concentrations than other contaminants) are detected while others are not detected. Detecting and identifying the composition or type of contamination is often needed to protect health and/or equipment, detect faults, and help identify the source or cause of the contamination. Inability to detect and identify the contamination may cause the need for a flight diversion, flight cancellation, or emergency landing to ensure the safety of passengers and crew, which, at a minimum, is an inconvenience, and increases costs.

There is a need for improved methods for detection and detection systems. The present invention provides for ameliorating at least some of the disadvantages of the prior art. These and other advantages of the present invention will be apparent from the description as set forth below.

BRIEF SUMMARY OF THE INVENTION

An embodiment of the invention provides a method for determining and classifying by type aircraft air contaminants, the method comprising: (a) passing aircraft air through an inlet of an aircraft air contaminant analyzer and through a flow-through heater block and a first valve, wherein the flow-through heater block is arranged to control temperature of the aircraft air passing through the flow-through heater block; passing a sample of the aircraft air through the aircraft air contaminant analyzer and through at least one aircraft air contaminant collector and a second valve along a first sample flow path at a first sample flow rate and/or at a first sample flow duration, while passing another sample of aircraft air through the aircraft air contaminant analyzer and through a bypass section and a third valve along a second sample flow path bypassing the at least one aircraft air contaminant collector at a second sample flow rate and/or at a second sample flow duration, the at least one aircraft air contaminant collector comprising: (i) a microporous medium comprising microporous flow-through channels arranged across the first sample flow path, the microporous medium having a chemoselective coating; and, (ii) a thin film resistive heater, capable of heating to a temperature that vaporizes captured air contaminants, wherein the heater is in contact with the microporous medium; the aircraft air contaminant analyzer also comprising a gravimetric sensor arranged to generate a proportionate resonant frequency response when air contaminant mass is added to or removed from the gravimetric sensor, for classifying air contaminant type; and wherein the bypass section comprising a bypass channel, the bypass channel including the second sample flow path; (a') the aircraft air contaminant analyzer further comprising: a pump generating flow along the first sample flow path and along the second sample flow path; a pressure sensor arranged between the first valve, the second valve, and the third valve; and a temperature sensor arranged to measure temperature in the flow-through heater block; (b) controlling the first sample flow rate and/or the first sample flow duration through the at least one aircraft air contaminant collector along the first sample flow path while independently controlling the second sample flow rate and/or the second sample flow duration through the bypass section along the second sample flow path, wherein the first sample flow rate and/or the first sample flow duration is/are initially set at a low value for a first measurement of response signal magnitude; (c) capturing air contaminants by the microporous medium; (d) closing the first valve and the second valve and when a desired pressure is reached based upon a signal from the pressure sensor, closing the third valve and discontinuing passing aircraft air through the at least one aircraft air contaminant collector along the first sample flow path; (e) heating the microporous medium to a temperature sufficient to vaporize the captured air contaminants and desorb the captured air contaminants; (f) receiving the desorbed air contaminants on the gravimetric sensor arranged to generate a proportionate resonant frequency response when air contaminant mass is added to or removed from the gravimetric sensor; (g) measuring the proportionate resonant frequency response generated by the gravimetric sensor as the air contaminant is added to and removed from the gravimetric sensor, determining the air contaminant concentration, classifying the air contaminant type, and outputting the determined air contaminant concentration and classified air contaminant type; (h) executing the air contaminant recognition program stored upon the computer-readable medium, including calculating air contaminant concentration using the measured signal magnitudes and first sample flow rates and the first sample flow durations along the first sample flow path; (i) opening the first valve, the second valve, and the third valve; (j) continuously repeating (b)-(i) and measuring response signal magnitudes and adjusting the first sample flow rate and/or the first sample flow duration based upon the previously measured signal magnitude such that the first sample flow rate and/or the first sample flow duration is increased when the signal magnitude is lower than the target level, by an amount proportionate to how much lower the signal magnitude is below the target level, to maintain the signal magnitude at the target level, and the first sample flow rate and/or the first sample flow duration is decreased when signal magnitude is higher than the target level, by an amount proportionate to how much higher the signal magnitude is above the target level, to maintain the signal magnitude at the target level; (k) executing the air contaminant recognition program stored upon the computer-readable medium, including calculating air contaminant concentration using the measured signal magnitudes and first sample flow rates and the first sample flow durations along the first sample flow path; and, (l) outputting the determined air contaminant concentration and air contaminant type.

Another embodiment of the invention provides a method for determining and classifying by type aircraft air contaminants, the method comprising (a) passing aircraft air through an inlet of an aircraft air contaminant analyzer and through a flow-through heater block and a first valve, wherein the flow-through heater block is arranged to control temperature of the aircraft air passing through the flow-through heater block; (a') the aircraft air contaminant analyzer comprising at least a first aircraft air contaminant collector and a second aircraft air contaminant collector; a first sample flow path including a first sample portion flow path and a second sample portion flow path; wherein the first aircraft air contaminant collector is arranged along the first sample portion flow path, the aircraft air contaminant analyzer including a first adjustable flow controller communicating with the first sample portion flow path; and the second aircraft air contaminant collector is arranged along the second sample portion flow path, the aircraft air contaminant analyzer including a second adjustable flow controller communicating with the second sample portion flow path; wherein the aircraft air contaminant analyzer includes a second valve arranged downstream of the first sample portion flow path and the second sample portion flow path; and, a bypass section providing a bypass sample flow path bypassing the first aircraft air contaminant collector and the first sample portion flow path, and bypassing the second aircraft air contaminant collector and the second sample portion flow path, the bypass section comprising a bypass channel, the bypass channel including the bypass sample flow path; wherein the aircraft air contaminant analyzer includes a third valve arranged downstream of the bypass sample flow path; the first aircraft air contaminant collector and the second aircraft air contaminant collector each separately comprising (i) a microporous medium comprising microporous flow through channels arranged across the sample portion flow path, the microporous medium having a chemoselective coating; and, (ii) a thin film resistive heater, capable of heating to a temperature that vaporizes captured air contaminants, wherein the heater is in contact with the microporous medium; the aircraft air contaminant analyzer also including gravimetric sensors near the first aircraft air contaminant collector and near the second aircraft air contaminant collector, each gravimetric sensor arranged to generate a proportionate resonant frequency response when air contaminant mass is added to or removed from the gravimetric sensor, for classifying air contaminant type; (a") the aircraft air contaminant analyzer further comprising a pump generating flow along the first sample portion flow path, the second sample portion flow path, and along the bypass sample flow path; a pressure sensor arranged between the first valve, the second valve, and the third valve; and a temperature sensor arranged to measure temperature in the flow through heater block; (b) passing a first sample of the aircraft air through the aircraft air contaminant analyzer and through the first and second aircraft air contaminant collectors and the second valve along the first sample flow path at a first sample flow rate and at a first sample flow duration, including passing a first sample portion of the first sample through the first aircraft air contaminant collector and passing a second sample portion of the first sample through the second aircraft air contaminant collector; passing the first sample portion of the aircraft air along the first sample portion flow path at a first sample portion flow rate and at a first sample portion flow duration, and passing the second sample portion of the aircraft air along the second sample portion flow path at a second sample portion flow rate and at a second sample portion flow duration, wherein the first sample portion flow duration equals the second sample portion flow duration; while passing another sample of aircraft air through the aircraft air contaminant analyzer and through the bypass section and a third valve along the bypass sample flow path bypassing the first and second aircraft air contaminant collectors at a bypass sample flow rate and at a bypass sample flow duration; (b') adjusting the first sample portion flow rate and the second sample portion flow rate such that the first sample portion flow rate is decreased by adjusting the first adjustable flow controller when a measured signal magnitude of the first aircraft contaminant collector is higher than a measured signal magnitude of the second aircraft contaminant collector; and the second sample portion flow rate is decreased by adjusting the second adjustable flow controller when a measured signal magnitude of the second aircraft contaminant collector is higher than a measured signal magnitude of the first aircraft contaminant collector; (c) controlling the first sample flow rate and/or the first sample flow duration along the first sample portion flow path; while independently controlling the bypass sample flow rate and/or the bypass sample flow duration through the bypass section along the bypass sample flow path; wherein the first sample flow rate and/or the first sample flow duration are initially set at a low value for initial measurements of response signal magnitudes; (d) capturing air contaminants by each microporous medium; (e) closing the first valve and the second valve and when a desired pressure is reached based upon a signal from the pressure sensor, closing the third valve and discontinuing passing aircraft air through the first and second aircraft air contaminant collector along the first sample portion flow path and the second sample portion flow path; (f) heating each microporous medium to a temperature sufficient to vaporize the captured air contaminants and desorb the captured air contaminants; (g) receiving the desorbed air contaminants on each gravimetric sensor arranged to generate a proportionate resonant frequency response when air contaminant mass is added to or removed from the gravimetric sensor; (h) measuring the proportionate resonant frequency response generated by each gravimetric sensor as the air contaminant is added to and removed from each gravimetric sensor, determining the signal magnitude from the proportionate resonant frequency response, determining the air contaminant concentration, classifying the air contaminant type, and outputting the determined air contaminant concentrations and classified air contaminant types; (i) executing the air contaminant recognition program stored upon the computer readable medium, including calculating air contaminant concentrations using the measured signal magnitudes and the first sample flow rates and the first sample flow duration along the first sample flow path; (j) opening the first valve, the second valve, and the third valve; (k) determining a target level for the signal magnitude, and continuously repeating (d)-(j) and measuring response signal magnitudes and adjusting the first sample flow rate and/or the first sample flow duration such that the first sample flow rate and/or the first sample flow duration is increased when the signal magnitude of either (iv) an average of the previously measured signal magnitudes by the gravimetric sensors near the first aircraft contaminant collector and near the second aircraft contaminant collector; or (v) the previously measured signal magnitude by the gravimetric sensor near the first aircraft contaminant collector; or (vi) the previously measured signal magnitude by the gravimetric sensor near the second aircraft contaminant collector is lower than a target level, by an amount proportionate to how much lower the measured signal magnitude is below the target level, to maintain the signal magnitude at the target level, and the first sample flow rate and/or the first sample flow duration is decreased when the measured signal magnitude of either (vii) the average of the previously measured signal magnitudes by the gravimetric sensors near the first aircraft contaminant collector and near the second aircraft contaminant collector; or (viii) the previously measured signal magnitude by the gravimetric sensor near the first aircraft contaminant collector; or (ix) the previously measured signal magnitude by the gravimetric sensor near the second aircraft contaminant collector is higher than the target level, by an amount proportionate to how much higher the signal magnitude is above the target level, to maintain the signal magnitude at the target level.

Yet another embodiment of the invention provides a method for determining and classifying by type aircraft air contaminants, the method comprising (a) passing aircraft air through an inlet of an aircraft air contaminant analyzer and through a flow-through heater block and a first valve, wherein the flow-through heater block is arranged to control temperature of the aircraft air passing through the flow-through heater block; passing a sample of the aircraft air through the aircraft air contaminant analyzer and through at least one aircraft air contaminant collector and a second valve along a first sample flow path at a first sample flow rate and/or at a first sample flow duration, while passing another sample of aircraft air through the aircraft air contaminant analyzer and through a bypass section and a third valve along a second sample flow path bypassing the at least one aircraft air contaminant collector at a second sample flow rate and/or at a second sample flow duration, the at least one aircraft air contaminant collector comprising (i) a microporous medium comprising microporous flow-through channels arranged across the first sample flow path, the microporous medium having a chemoselective coating; and, (ii) a thin film resistive heater, capable of heating to a temperature that vaporizes captured air contaminants, wherein the heater is in contact with the microporous medium; the aircraft air contaminant analyzer also including a gravimetric sensor arranged to generate a proportionate resonant frequency response when air contaminant mass is added to or removed from the gravimetric sensor, for classifying air contaminant type; and wherein the bypass section comprising a bypass channel, the bypass channel including the second sample flow path; (a') the aircraft air contaminant analyzer further comprising a pump generating flow along the first sample flow path and along the second sample flow path; a pressure sensor arranged between the first valve, the second valve, and the third valve; and a temperature sensor arranged to measure temperature in the flow-through heater block; (b) controlling the first sample flow rate and/or the first sample flow duration through the at least one aircraft air contaminant collector along the first sample flow path while independently controlling the second sample flow rate and/or the second sample flow duration through the bypass section along the second sample flow path, wherein the first sample flow rate and/or the first sample flow duration is/are initially set at a low value for a first measurement of response signal magnitude; (c) capturing air contaminants by the microporous medium; (d) closing the first valve and the second valve and when a desired pressure is reached based upon a signal from the pressure sensor, closing the third valve and discontinuing passing aircraft air through the at least one aircraft air contaminant collector along the first sample flow path; (e) heating the microporous medium to a temperature sufficient to vaporize the captured air contaminants and desorb the captured air contaminants; (f) receiving the desorbed air contaminants on the gravimetric sensor arranged to generate a proportionate resonant frequency response when air contaminant mass is added to or removed from the gravimetric sensor; (g) measuring the proportionate resonant frequency response generated by the gravimetric sensor as the air contaminant is added to and removed from the gravimetric sensor, determining the signal magnitude from the proportionate resonant frequency response, determining the air contaminant concentration, classifying the air contaminant type, and outputting the determined air contaminant concentration and classified air contaminant type; (h) executing the air contaminant recognition program stored upon the computer-readable medium, including calculating air contaminant concentration using the measured signal magnitudes and first sample flow rates and the first sample flow durations along the first sample flow path; (i) opening the first valve, the second valve, and the third valve; (j) determining the upper threshold and the lower threshold for the signal magnitude for the contaminant type, and continuously repeating (b)-(i) and measuring response signal magnitudes and adjusting the first sample flow rate and/or the first sample flow duration based upon the previously measured signal magnitude such that the first sample flow rate and/or the first sample flow duration is increased when the signal magnitude is lower than the lower threshold, to the next pre-determined higher sensitivity level, to maintain the signal magnitude between the upper threshold and the lower threshold, and the first sample flow rate and/or the first sample flow duration is decreased when signal magnitude is higher than the upper threshold, to the next pre-determined lower sensitivity level, to maintain the signal magnitude between the upper threshold and the lower threshold; (k) executing the air contaminant recognition program stored upon the computer-readable medium, including calculating air contaminant concentration using the measured signal magnitudes and first sample flow rates and the first sample flow durations along the first sample flow path; and, (l) outputting the determined air contaminant concentration and air contaminant type.

Still another embodiment of the invention provides a method for determining and classifying by type aircraft air contaminants, the method comprising (a) passing aircraft air through an inlet of an aircraft air contaminant analyzer and through a flow-through heater block and a first valve, wherein the flow-through heater block is arranged to control temperature of the aircraft air passing through the flow-through heater block; (a') the aircraft air contaminant analyzer comprising at least a first aircraft air contaminant collector and a second aircraft air contaminant collector; a first sample flow path including a first sample portion flow path and a second sample portion flow path; wherein the first aircraft air contaminant collector is arranged along the first sample portion flow path, the aircraft air contaminant analyzer including a first adjustable flow controller communicating with the first sample portion flow path; and the second aircraft air contaminant collector is arranged along the second sample portion flow path, the aircraft air contaminant analyzer including a second adjustable flow controller communicating with the second sample portion flow path; wherein the aircraft air contaminant analyzer includes a second valve arranged downstream of the first sample portion flow path and the second sample portion flow path; and, a bypass section providing a bypass sample flow path bypassing the first aircraft air contaminant collector and the first sample portion flow path, and bypassing the second aircraft air contaminant collector and the second sample portion flow path, the bypass section comprising a bypass channel, the bypass channel including the bypass sample flow path; wherein the aircraft air contaminant analyzer includes a third valve arranged downstream of the bypass sample flow path; the first aircraft air contaminant collector and the second aircraft air contaminant collector each separately comprising (i) a microporous medium comprising microporous flow through channels arranged across the sample portion flow path, the microporous medium having a chemoselective coating; and, (ii) a thin film resistive heater, capable of heating to a temperature that vaporizes captured air contaminants, wherein the heater is in contact with the microporous medium; the aircraft air contaminant analyzer also including gravimetric sensors near the first aircraft air contaminant collector and near the second aircraft air contaminant collector, each gravimetric sensor arranged to generate a proportionate resonant frequency response when air contaminant mass is added to or removed from the gravimetric sensor, for classifying air contaminant type; (a″) the aircraft air contaminant analyzer further comprising a pump generating flow along the first sample portion flow path, the second sample portion flow path, and along the bypass sample flow path; a pressure sensor arranged between the first valve, the second valve, and the third valve; and a temperature sensor arranged to measure temperature in the flow through heater block; (b) passing a first sample of the aircraft air through the aircraft air contaminant analyzer and through the first and second aircraft air contaminant collectors and the second valve along the first sample flow path at a first sample flow rate and at a first sample flow duration, including passing a first sample portion of the first sample through the first aircraft air contaminant collector and passing a second sample portion of the first sample through the second aircraft air contaminant collector; passing the first sample portion of the aircraft air along the first sample portion flow path at a first sample portion flow rate and at a first sample portion flow duration, and passing the second sample portion of the aircraft air along the second sample portion flow path at a second sample portion flow rate and at a second sample portion flow duration, wherein the first sample portion flow duration equals the second sample portion flow duration; while passing another sample of aircraft air through the aircraft air contaminant analyzer and through the bypass section and a third valve along the bypass sample flow path bypassing the first and second aircraft air contaminant collectors at a bypass sample flow rate and at a bypass sample flow duration; (b') adjusting the first sample portion flow rate and the second sample portion flow rate such that the first sample portion flow rate is decreased by adjusting the first adjustable flow controller when a measured signal magnitude of the first aircraft contaminant collector is higher than a measured signal magnitude of the second aircraft contaminant collector; and the second sample portion flow rate is decreased by adjusting the second adjustable flow controller when a measured signal magnitude of the second aircraft contaminant collector is higher than a measured signal magnitude of the first aircraft contaminant collector; (c) controlling the first sample flow rate and/or the first sample flow duration along the first sample portion flow path; while independently controlling the bypass sample flow rate and/or the bypass sample flow duration through the bypass section along the bypass sample flow path; wherein the first sample flow rate and/or the first sample flow duration are initially set at a low value for initial measurements of response signal magnitudes; (d) capturing air contaminants by each microporous medium; (e) closing the first valve and the second valve and when a desired pressure is reached based upon a signal from the pressure sensor, closing the third valve and discontinuing passing aircraft air through the first and second aircraft air contaminant collector along the first sample portion flow path and the second sample portion flow path; (f) heating each microporous medium to a temperature sufficient to vaporize the captured air contaminants and desorb the captured air contaminants; (g) receiving the desorbed air contaminants on each gravimetric sensor arranged to generate a proportionate resonant frequency response when air contaminant mass is added to or removed from the gravimetric sensor; (h) measuring the proportionate resonant frequency response generated by each gravimetric sensor as the air contaminant is added to and removed from each gravimetric sensor, determining the signal magnitude from the proportionate resonant frequency response, determining the air contaminant concentration, classifying the air contaminant type, and outputting the determined air contaminant concentrations and classified air contaminant types; (i) executing the air contaminant recognition program stored upon the computer readable medium, including calculating air contaminant concentrations using the measured signal magnitudes and the first sample flow rates and the first sample portion flow duration along the first sample flow path; (j) opening the first valve, the second valve, and the third valve; (k) determining the upper threshold and the lower threshold for the signal magnitude for the contaminant type, and continuously repeating (d)-(j) and measuring response signal magnitudes and adjusting the first sample flow rate and/or the first sample flow duration such that the first sample flow rate and/or the first sample flow duration is increased when the signal magnitude of either (iv) an average of the previously measured signal magnitudes by the gravimetric sensors near the first aircraft contaminant collector and near the second aircraft contaminant collector; or (v) the previously measured signal magnitude by the gravimetric sensor near the first aircraft contaminant collector; or (vi) the previously measured signal magnitude of the gravimetric sensor near the second aircraft contaminant collector is lower than the lower threshold, to the next pre-determined higher sensitivity level, to maintain the signal magnitude at between the lower threshold and the upper threshold; and the first sample flow rate and/or the first sample flow duration is decreased when the measured signal magnitude of either (vii) the average of the previously measured signal magnitudes of the first aircraft contaminant collector and second aircraft contaminant collector; or (viii) the previously measured signal magnitude of the first aircraft contaminant collector; or (ix) the previously measured signal magnitude of the second aircraft contaminant collector is higher than the than the upper threshold, to the next pre-determined lower sensitivity level, to maintain the signal magnitude to maintain the signal magnitude between the upper threshold and the lower threshold.

In another embodiment, an aircraft air contaminant analyzer is provided comprising (a) at least one aircraft air contaminant collector comprising (i) a microporous medium comprising microporous flow-through channels and a chemoselective coating, wherein the microporous medium remains functional and desorbs captured air contaminants while being heated for a controlled time period, the at least one aircraft contaminant collector providing a first sample flow path, wherein the microporous medium is arranged across the first sample flow path; (ii) a thin film resistive heater, capable of heating to a temperature that vaporizes captured air contaminants, wherein the heater is in contact with the microporous medium; (b) a bypass section, comprising a bypass channel, the bypass channel including a second sample flow path, the bypass channel bypassing the at least one aircraft air contaminant collector; (c) a first substrate, having a top surface and a bottom surface; wherein the at least one contaminant collector is associated with the first substrate, the microporous medium and heater being thermally insulated from the first substrate; (d) a gravimetric sensor arranged to generate a proportionate resonant frequency response when air contaminant mass is added to or removed from the gravimetric sensor, for classifying air contaminant type; (e) a second substrate, having a top surface and a bottom surface; wherein the gravimetric sensor is associated with the top surface of the second substrate, the gravimetric sensor being separated from the contaminant collector by a constant distance, the gravimetric sensor being arranged to receive air contaminants desorbed from the membrane when the membrane is heated; (f) a support comprising a top surface and a bottom surface, the support comprising a common inlet port passing through the top surface and the bottom surface of the support, wherein the bottom surface of the second substrate is associated with the top surface of the support; the aircraft air contaminant analyzer further comprising an aircraft air contaminant inlet port; a flow-through heater block; and a first valve, arranged upstream of the common inlet port; a second valve, downstream of the at least one aircraft air contaminant collector, and arranged along the first sample flow path; a third valve arranged along the second sample flow path; a pump arranged to generate flow along the first sample flow path and along the second sample flow path; a pressure sensor arranged between the first valve, the second valve, and the third valve; and a temperature sensor arranged to measure temperature in the flow-through heater block; (h) a resonant frequency measurement device, arranged to measure the proportionate resonant frequency response generated by the gravimetric sensor as the air contaminant is added to and removed from the gravimetric sensor; (i) a computer readable medium bearing an air contaminant recognition program and calibration data; and (j) a processor configured: to execute the air contaminant recognition program, the contaminant recognition program including a module configured to classify the air contaminant by type, and to measure response signal magnitudes from the proportionate resonant frequency response generated by the gravimetric sensor, and a module programmed to use the calibration data for comparison with the signal magnitude to calculate air contaminant concentration; and, to execute a sensitivity control program, the sensitivity control program including a module configured to maintain the signal magnitude at a predetermined target level or within a predetermined upper threshold and a predetermined lower threshold, by controlling the first valve, the second valve, and/or the third valve and/or the pump to: increase the first sample flow rates and/or the first sample flow durations when the signal magnitude is less than the predetermined target level or the predetermined lower threshold; decrease the first sample flow rates and/or the first sample flow durations when the proportionate resonant frequency response is greater than the predetermined target level or the predetermined upper threshold.

In some embodiments, the aircraft air contaminant analyzer further comprises an additional aircraft air contaminant collector such that the analyzer comprises a first aircraft air contaminant collector and a second aircraft air contaminant collector; the first sample flow path including a first sample portion flow path and a second sample portion flow path; wherein the first aircraft air contaminant collector is arranged along the first sample portion flow path, the aircraft air contaminant analyzer including a first adjustable flow controller communicating with the first sample portion flow path; and the second aircraft air contaminant collector is arranged along the second sample portion flow path, the aircraft air contaminant analyzer including a second adjustable flow controller communicating with the second sample portion flow path; wherein the aircraft air contaminant analyzer includes the second valve arranged downstream of the first sample portion flow path and the second sample portion flow path; and, wherein the bypass section providing the second sample flow path bypasses the first aircraft air contaminant collector and the first sample portion flow path, and bypasses the second aircraft air contaminant collector and the second sample portion flow path and wherein the third valve is arranged downstream of the second sample flow path; the first aircraft air contaminant collector and the second aircraft air contaminant collector each separately comprising (i) a microporous medium comprising microporous flow through channels arranged across the sample portion flow path, the microporous medium having a chemoselective coating; and, (ii) a thin film resistive heater, capable of heating to a temperature that vaporizes captured air contaminants, wherein the heater is in contact with the microporous medium; the aircraft air contaminant analyzer also including a gravimetric sensor arranged near each respective aircraft air contaminant collector to generate a proportionate resonant frequency response when air contaminant mass is added to or removed from the respective gravimetric sensor, for classifying air contaminant type; the pump generating flow along the first sample portion flow path, the second sample portion flow path, and along the second sample flow path; wherein the air contaminant recognition program includes a module configured to measure response signal magnitudes from the proportionate resonant frequency responses generated by the gravimetric sensors near each respective collector, and a module to calculate air contaminant concentrations using one or both signal magnitudes, wherein the sensitivity control program includes a module configured to maintain either an average of the previously measured signal magnitudes by the gravimetric sensors near the first aircraft contaminant collector and near the second aircraft contaminant collector; or the previously measured signal magnitude of the gravimetric sensor near the first aircraft contaminant collector; or the previously measured signal magnitude of the gravimetric sensor near the second aircraft contaminant collector, at a predetermined target level or within a predetermined upper threshold and a predetermined lower threshold, by controlling the first valve, the second valve, and/or the third valve and/or the pump to: increase the first sample flow rates and/or the first sample flow durations when the signal magnitude is less than the predetermined target level or the predetermined lower threshold; decrease the first sample flow rates and/or the first sample flow durations when the signal magnitude is greater than the predetermined target level or the predetermined upper threshold.

BRIEF DESCRIPTION OF THE SEVERAL VIEWS OF THE DRAWING(S)

FIG. 1 is a diagrammatic top view of two aircraft air collectors of an illustrative air craft air contaminant analyzer according to an embodiment of the invention.

FIG. 2 is a diagrammatic representation of an illustrative air craft air contaminant analyzer according to an embodiment of the invention along line A-A of FIG. 1, including a pump, and one of the two aircraft air contaminant collectors, the illustrated aircraft air contaminant collector comprising a microporous medium comprising microporous flow-through channels and a chemoselective coating, and a heater in contact with the microporous medium, provided along a first sample portion flow path; the aircraft air contaminant analyzer also comprising a gravimetric sensor; and a bypass section comprising a bypass channel, providing a bypass sample flow path bypassing the aircraft air contaminant collector, wherein the pump generates sample flow along the first sample portion flow path and the bypass sample flow path.

FIG. 3 is a diagrammatic representation of an illustrative air craft air contaminant analyzer according to an embodiment of the invention along line B-B of FIG. 1, including the pump, and two gravimetric sensors, and two aircraft air contaminant collectors, each aircraft air contaminant collector comprising a microporous medium comprising microporous flow-through channels and a chemoselective coating, and a heater, wherein each heater is in contact with a microporous medium, provided along a first sample portion flow path and a second sample portion flow path; wherein the pump generates sample flow along the first sample portion flow path and the second sample portion flow path.

FIG. 4A is a diagrammatic top view of an embodiment of the air contaminant collector shown in FIG. 2, showing the microporous membrane, also showing a chemoselective coating on the membrane, and the thin film resistive heater, also showing a base, and tethers, wherein the tethers connect the microporous membrane to the base. FIG. 4B is a diagrammatic enlarged view of a portion of the embodiment of the air contaminant collector shown in FIG. 4A, showing channels in the base providing tethers for connecting the microporous membrane to the base, also showing the thin film resistive heater associated with the top surface of the microporous membrane (surrounding the flow-through channels of the microporous membrane), and on the tethers, also showing electrical traces and the chemoselective coating, wherein only portions of the coating and the heater are shown so that other components can also be shown. FIG. 4C shows an enlarged view of the bottom surface of the microporous membrane, also showing the bottom surfaces of the tethers connecting the microporous membrane to the base. FIG. 4D is a diagrammatic cross-sectional view of an embodiment of the air contaminant collector with the coating, also showing electrical traces, and an insulator layer, wherein the traces are on top of the heater and insulating layer, and the insulating layer forms the top surface of the microporous membrane.

DETAILED DESCRIPTION OF THE INVENTION

Figure 1:
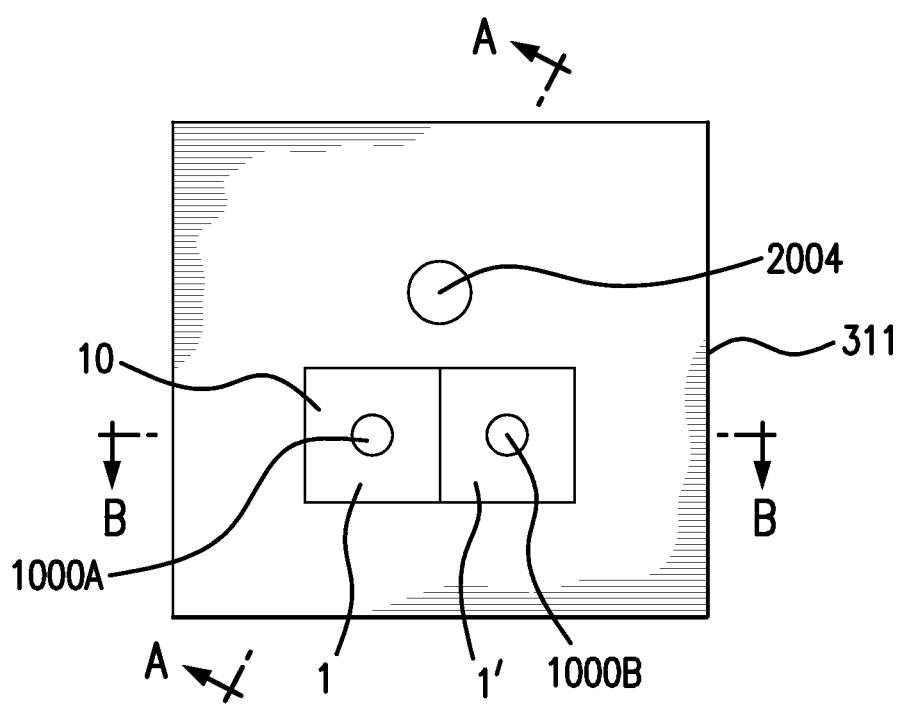

An embodiment of the invention provides a method for determining and classifying by type aircraft air contaminants, the method comprising: (a) passing aircraft air through an inlet of an aircraft air contaminant analyzer and through a flow-through heater block and a first valve, wherein the flow-through heater block is arranged to control temperature of the aircraft air passing through the flow-through heater block; passing a sample of the aircraft air through the aircraft air contaminant analyzer and through at least one aircraft air contaminant collector and a second valve along a first sample flow path at a first sample flow rate and/or at a first sample flow duration, while passing another sample of aircraft air through the aircraft air contaminant analyzer and through a bypass section and a third valve along a second sample flow path bypassing the at least one aircraft air contaminant collector at a second sample flow rate and/or at a second sample flow duration, the at least one aircraft air contaminant collector comprising: (i) a microporous medium comprising microporous flow-through channels arranged across the first sample flow path, the microporous medium having a chemoselective coating; and, (ii) a thin film resistive heater, capable of heating to a temperature that vaporizes captured air contaminants, wherein the heater is in contact with the microporous medium; the aircraft air contaminant analyzer also comprising a gravimetric sensor arranged to generate a proportionate resonant frequency response when air contaminant mass is added to or removed from the gravimetric sensor, for classifying air contaminant type; and wherein the bypass section comprising a bypass channel, the bypass channel including the second sample flow path; (a') the aircraft air contaminant analyzer further comprising: a pump generating flow along the first sample flow path and along the second sample flow path; a pressure sensor arranged between the first valve, the second valve, and the third valve; and a temperature sensor arranged to measure temperature in the flow-through heater block; (b) controlling the first sample flow rate and/or the first sample flow duration through the at least one aircraft air contaminant collector along the first sample flow path while independently controlling the second sample flow rate and/or the second sample flow duration through the bypass section along the second sample flow path, wherein the first sample flow rate and/or the first sample flow duration is/are initially set at a low value for a first measurement of response signal magnitude; (c) capturing air contaminants by the microporous medium; (d) closing the first valve and the second valve and when a desired pressure is reached based upon a signal from the pressure sensor, closing the third valve and discontinuing passing aircraft air through the at least one aircraft air contaminant collector along the first sample flow path; (e) heating the microporous medium to a temperature sufficient to vaporize the captured air contaminants and desorb the captured air contaminants; (f) receiving the desorbed air contaminants on the gravimetric sensor arranged to generate a proportionate resonant frequency response when air contaminant mass is added to or removed from the gravimetric sensor; (g) measuring the proportionate resonant frequency response generated by the gravimetric sensor as the air contaminant is added to and removed from the gravimetric sensor, determining the air contaminant concentration, classifying the air contaminant type, and outputting the determined air contaminant concentration and classified air contaminant type; (h) executing the air contaminant recognition program stored upon the computer-readable medium, including calculating air contaminant concentration using the measured signal magnitudes and first sample flow rates and the first sample flow durations along the first sample flow path; (i) opening the first valve, the second valve, and the third valve; (j) continuously repeating (b)-(i) and measuring response signal magnitudes and adjusting the first sample flow rate and/or the first sample flow duration based upon the previously measured signal magnitude such that the first sample flow rate and/or the first sample flow duration is increased when the signal magnitude is lower than the target level, by an amount proportionate to how much lower the signal magnitude is below the target level, to maintain the signal magnitude at the target level, and the first sample flow rate and/or the first sample flow duration is decreased when signal magnitude is higher than the target level, by an amount proportionate to how much higher the signal magnitude is above the target level, to maintain the signal magnitude at the target level; (k) executing the air contaminant recognition program stored upon the computer-readable medium, including calculating air contaminant concentration using the measured signal magnitudes and first sample flow rates and the first sample flow durations along the first sample flow path; and, (l) outputting the determined air contaminant concentration and air contaminant type.

Another embodiment of the invention provides a method for determining and classifying by type aircraft air contaminants, the method comprising (a) passing aircraft air through an inlet of an aircraft air contaminant analyzer and through a flow-through heater block and a first valve, wherein the flow-through heater block is arranged to control temperature of the aircraft air passing through the flow-through heater block; (a') the aircraft air contaminant analyzer comprising at least a first aircraft air contaminant collector and a second aircraft air contaminant collector; a first sample flow path including a first sample portion flow path and a second sample portion flow path; wherein the first aircraft air contaminant collector is arranged along the first sample portion flow path, the aircraft air contaminant analyzer including a first adjustable flow controller communicating with the first sample portion flow path; and the second aircraft air contaminant collector is arranged along the second sample portion flow path, the aircraft air contaminant analyzer including a second adjustable flow controller communicating with the second sample portion flow path; wherein the aircraft air contaminant analyzer includes a second valve arranged downstream of the first sample portion flow path and the second sample portion flow path; and, a bypass section providing a bypass sample flow path bypassing the first aircraft air contaminant collector and the first sample portion flow path, and bypassing the second aircraft air contaminant collector and the second sample portion flow path, the bypass section comprising a bypass channel, the bypass channel including the bypass sample flow path; wherein the aircraft air contaminant analyzer includes a third valve arranged downstream of the bypass sample flow path; the first aircraft air contaminant collector and the second aircraft air contaminant collector each separately comprising (i) a microporous medium comprising microporous flow through channels arranged across the sample portion flow path, the microporous medium having a chemoselective coating; and, (ii) a thin film resistive heater, capable of heating to a temperature that vaporizes captured air contaminants, wherein the heater is in contact with the microporous medium; the aircraft air contaminant analyzer also including a gravimetric sensor near the first aircraft air contaminant collector and near the second aircraft air contaminant collector, each gravimetric sensor arranged to generate a proportionate resonant frequency response when air contaminant mass is added to or removed from the gravimetric sensor, for classifying air contaminant type; (a″) the aircraft air contaminant analyzer further comprising a pump generating flow along the first sample portion flow path, the second sample portion flow path, and along the bypass sample flow path; a pressure sensor arranged between the first valve, the second valve, and the third valve; and a temperature sensor arranged to measure temperature in the flow through heater block; (b) passing a first sample of the aircraft air through the aircraft air contaminant analyzer and through the first and second aircraft air contaminant collectors and the second valve along the first sample flow path at a first sample flow rate and at a first sample flow duration, including passing a first sample portion of the first sample through the first aircraft air contaminant collector and passing a second sample portion of the first sample through the second aircraft air contaminant collector; passing the first sample portion of the aircraft air along the first sample portion flow path at a first sample portion flow rate and at a first sample portion flow duration, and passing the second sample portion of the aircraft air along the second sample portion flow path at a second sample portion flow rate and at a second sample portion flow duration, wherein the first sample portion flow duration equals the second sample portion flow duration; while passing another sample of aircraft air through the aircraft air contaminant analyzer and through the bypass section and a third valve along the bypass sample flow path bypassing the first and second aircraft air contaminant collectors at a bypass sample flow rate and at a bypass sample flow duration; (b') adjusting the first sample portion flow rate and the second sample portion flow rate such that the first sample portion flow rate is decreased by adjusting the first adjustable flow controller when a measured signal magnitude by the gravimetric sensor near the first aircraft contaminant collector is higher than a measured signal magnitude by the gravimetric sensor near the second aircraft contaminant collector; and the second sample portion flow rate is decreased by adjusting the second adjustable flow controller when a measured signal magnitude by the gravimetric sensor near the second aircraft contaminant collector is higher than a measured signal magnitude by the gravimetric sensor near the first aircraft contaminant collector; (c) controlling the first sample flow rate and/or the first sample flow duration along the first sample portion flow path; while independently controlling the bypass sample flow rate and/or the bypass sample flow duration through the bypass section along the bypass sample flow path; wherein the first sample flow rate and/or the first sample flow duration are initially set at a low value for initial measurements of response signal magnitudes; (d) capturing air contaminants by each microporous medium; (e) closing the first valve and the second valve and when a desired pressure is reached based upon a signal from the pressure sensor, closing the third valve and discontinuing passing aircraft air through the first and second aircraft air contaminant collector along the first sample portion flow path and the second sample portion flow path; (f) heating each microporous medium to a temperature sufficient to vaporize the captured air contaminants and desorb the captured air contaminants; (g) receiving the desorbed air contaminants on each gravimetric sensor arranged to generate a proportionate resonant frequency response when air contaminant mass is added to or removed from the gravimetric sensor; (h) measuring the proportionate resonant frequency response generated by each gravimetric sensor as the air contaminant is added to and removed from each gravimetric sensor, determining the signal magnitude from the proportionate resonant frequency response, determining the air contaminant concentration, classifying the air contaminant type, and outputting the determined air contaminant concentrations and classified air contaminant types; (i) executing the air contaminant recognition program stored upon the computer readable medium, including calculating air contaminant concentrations using the measured signal magnitudes and the first sample portion flow rates and the first sample portion flow durations along the first sample portion flow path and the second sample portion flow rates and the second sample portion flow durations along the second sample portion flow path; (j) opening the first valve, the second valve, and the third valve; (k) determining a target level for the signal magnitude, and continuously repeating (d)-(j) and measuring response signal magnitudes and adjusting the first sample flow rate and/or the first sample flow duration such that the first sample flow rate and/or the first sample flow duration is increased when the signal magnitude of either (iv) an average of the previously measured signal magnitudes by the gravimetric sensors near the first aircraft contaminant collector and near the second aircraft contaminant collector; or (v) the previously measured signal magnitude by the gravimetric sensor near the first aircraft contaminant collector; or (vi) the previously measured signal magnitude by the gravimetric sensor near the second aircraft contaminant collector is lower than a target level, by an amount proportionate to how much lower the measured signal magnitude is below the target level, to maintain the signal magnitude at the target level, and the first sample flow rate and/or the first sample flow duration is decreased when the measured signal magnitude of either (vii) the average of the previously measured signal magnitudes by the gravimetric sensors near the first aircraft contaminant collector and near the second aircraft contaminant collector; or (viii) the previously measured signal magnitude by the gravimetric sensor near the first aircraft contaminant collector; or (ix) the previously measured signal magnitude by the gravimetric sensor near the second aircraft contaminant collector is higher than the target level, by an amount proportionate to how much higher the signal magnitude is above the target level, to maintain the signal magnitude at the target level.

Yet another embodiment of the invention provides a method for determining and classifying by type aircraft air contaminants, the method comprising (a) passing aircraft air through an inlet of an aircraft air contaminant analyzer and through a flow-through heater block and a first valve, wherein the flow-through heater block is arranged to control temperature of the aircraft air passing through the flow-through heater block; passing a sample of the aircraft air through the aircraft air contaminant analyzer and through at least one aircraft air contaminant collector and a second valve along a first sample flow path at a first sample flow rate and/or at a first sample flow duration, while passing another sample of aircraft air through the aircraft air contaminant analyzer and through a bypass section and a third valve along a second sample flow path bypassing the at least one aircraft air contaminant collector at a second sample flow rate and/or at a second sample flow duration, the at least one aircraft air contaminant collector comprising (i) a microporous medium comprising microporous flow-through channels arranged across the first sample flow path, the microporous medium having a chemoselective coating; and, (ii) a thin film resistive heater, capable of heating to a temperature that vaporizes captured air contaminants, wherein the heater is in contact with the microporous medium; the aircraft air contaminant analyzer also including a gravimetric sensor arranged to generate a proportionate resonant frequency response when air contaminant mass is added to or removed from the gravimetric sensor, for classifying air contaminant type; and wherein the bypass section comprising a bypass channel, the bypass channel including the second sample flow path; (a') the aircraft air contaminant analyzer further comprising a pump generating flow along the first sample flow path and along the second sample flow path; a pressure sensor arranged between the first valve, the second valve, and the third valve; and a temperature sensor arranged to measure temperature in the flow-through heater block; (b) controlling the first sample flow rate and/or the first sample flow duration through the at least one aircraft air contaminant collector along the first sample flow path while independently controlling the second sample flow rate and/or the second sample flow duration through the bypass section along the second sample flow path, wherein the first sample flow rate and/or the first sample flow duration is/are initially set at a low value for a first measurement of response signal magnitude; (c) capturing air contaminants by the microporous medium; (d) closing the first valve and the second valve and when a desired pressure is reached based upon a signal from the pressure sensor, closing the third valve and discontinuing passing aircraft air through the at least one aircraft air contaminant collector along the first sample flow path; (e) heating the microporous medium to a temperature sufficient to vaporize the captured air contaminants and desorb the captured air contaminants; (f) receiving the desorbed air contaminants on the gravimetric sensor arranged to generate a proportionate resonant frequency response when air contaminant mass is added to or removed from the gravimetric sensor; (g) measuring the proportionate resonant frequency response generated by the gravimetric sensor as the air contaminant is added to and removed from the gravimetric sensor, determining the signal magnitude from the proportionate resonant frequency response, determining the air contaminant concentration, classifying the air contaminant type, and outputting the determined air contaminant concentration and classified air contaminant type; (h) executing the air contaminant recognition program stored upon the computer-readable medium, including calculating air contaminant concentration using the measured signal magnitudes and first sample flow rates and the first sample flow durations along the first sample flow path; (i) opening the first valve, the second valve, and the third valve; (j) determining the upper threshold and the lower threshold for the signal magnitude for the contaminant type, and continuously repeating (b)-(i) and measuring response signal magnitudes and adjusting the first sample flow rate and/or the first sample flow duration based upon the previously measured signal magnitude such that the first sample flow rate and/or the first sample flow duration is increased when the signal magnitude is lower than the lower threshold, to the next pre-determined higher sensitivity level, to maintain the signal magnitude between the upper threshold and the lower threshold, and the first sample flow rate and/or the first sample flow duration is decreased when signal magnitude is higher than the upper threshold, to the next pre-determined lower sensitivity level, to maintain the signal magnitude between the upper threshold and the lower threshold; (k) executing the air contaminant recognition program stored upon the computer-readable medium, including calculating air contaminant concentration using the measured signal magnitudes and first sample flow rates and the first sample flow durations along the first sample flow path; and, (l) outputting the determined air contaminant concentration and air contaminant type.

Still another embodiment of the invention provides a method for determining and classifying by type aircraft air contaminants, the method comprising (a) passing aircraft air through an inlet of an aircraft air contaminant analyzer and through a flow-through heater block and a first valve, wherein the flow-through heater block is arranged to control temperature of the aircraft air passing through the flow-through heater block; (a') the aircraft air contaminant analyzer comprising at least a first aircraft air contaminant collector and a second aircraft air contaminant collector; a first sample flow path including a first sample portion flow path and a second sample portion flow path; wherein the first aircraft air contaminant collector is arranged along the first sample portion flow path, the aircraft air contaminant analyzer including a first adjustable flow controller communicating with the first sample portion flow path; and the second aircraft air contaminant collector is arranged along the second sample portion flow path, the aircraft air contaminant analyzer including a second adjustable flow controller communicating with the second sample portion flow path; wherein the aircraft air contaminant analyzer includes a second valve arranged downstream of the first sample portion flow path and the second sample portion flow path; and, a bypass section providing a bypass sample flow path bypassing the first aircraft air contaminant collector and the first sample portion flow path, and bypassing the second aircraft air contaminant collector and the second sample portion flow path, the bypass section comprising a bypass channel, the bypass channel including the bypass sample flow path; wherein the aircraft air contaminant analyzer includes a third valve arranged downstream of the bypass sample flow path; the first aircraft air contaminant collector and the second aircraft air contaminant collector each separately comprising (i) a microporous medium comprising microporous flow through channels arranged across the sample portion flow path, the microporous medium having a chemoselective coating; and, (ii) a thin film resistive heater, capable of heating to a temperature that vaporizes captured air contaminants, wherein the heater is in contact with the microporous medium; the aircraft air contaminant analyzer also including a gravimetric sensor arranged to generate a proportionate resonant frequency response when air contaminant mass is added to or removed from the gravimetric sensor, for classifying air contaminant type; (a") the aircraft air contaminant analyzer further comprising: a pump generating flow along the first sample portion flow path, the second sample portion flow path, and along the bypass sample flow path; a pressure sensor arranged between the first valve, the second valve, and the third valve; and a temperature sensor arranged to measure temperature in the flow through heater block; (b) passing a first sample of the aircraft air through the aircraft air contaminant analyzer and through the first and second aircraft air contaminant collectors and the second valve along the first sample flow path at a first sample flow rate and at a first sample flow duration, including passing a first sample portion of the first sample through the first aircraft air contaminant collector and passing a second sample portion of the first sample through the second aircraft air contaminant collector; passing the first sample portion of the aircraft air along the first sample portion flow path at a first sample portion flow rate and at a first sample portion flow duration, and passing the second sample portion of the aircraft air along the second sample portion flow path at a second sample portion flow rate and at a second sample portion flow duration, wherein the first sample portion flow duration equals the second sample portion flow duration; while passing another sample of aircraft air through the aircraft air contaminant analyzer and through the bypass section and a third valve along the bypass sample flow path bypassing the first and second aircraft air contaminant collectors at a bypass sample flow rate and at a bypass sample flow duration; (b') adjusting the first sample portion flow rate and the second sample portion flow rate such that the first sample portion flow rate is decreased by adjusting the first adjustable flow controller when a measured signal magnitude of the first aircraft contaminant collector is higher than a measured signal magnitude of the second aircraft contaminant collector; and the second sample portion flow rate is decreased by adjusting the second adjustable flow controller when a measured signal magnitude of the second aircraft contaminant collector is higher than a measured signal magnitude of the first aircraft contaminant collector; (c) controlling the first sample flow rate and/or the first sample flow duration along the first sample portion flow path; while independently controlling the bypass sample flow rate and/or the bypass sample flow duration through the bypass section along the bypass sample flow path; wherein the first sample flow rate and/or the first sample flow duration are initially set at a low value for initial measurements of response signal magnitudes; (d) capturing air contaminants by each microporous medium; (e) closing the first valve and the second valve and when a desired pressure is reached based upon a signal from the pressure sensor, closing the third valve and discontinuing passing aircraft air through the first and second aircraft air contaminant collector along the first sample portion flow path and the second sample portion flow path; (f) heating each microporous medium to a temperature sufficient to vaporize the captured air contaminants and desorb the captured air contaminants; (g) receiving the desorbed air contaminants on each gravimetric sensor arranged to generate a proportionate resonant frequency response when air contaminant mass is added to or removed from the gravimetric sensor; (h) measuring the proportionate resonant frequency response generated by each gravimetric sensor as the air contaminant is added to and removed from each gravimetric sensor, determining the signal magnitude from the proportionate resonant frequency response, determining the air contaminant concentration, classifying the air contaminant type, and outputting the determined air contaminant concentrations and classified air contaminant types; (i) executing the air contaminant recognition program stored upon the computer readable medium, including calculating air contaminant concentrations using the measured signal magnitudes and the first sample flow rates and the first sample flow duration along the first sample flow path; (j) opening the first valve, the second valve, and the third valve; (k) determining the upper threshold and the lower threshold for the signal magnitude for the contaminant type, and continuously repeating (d)-(j) and measuring response signal magnitudes and adjusting the first sample flow rate and/or the first sample flow duration such that the first sample flow rate and/or the first sample flow duration is increased when the signal magnitude of either (iv) an average of the previously measured signal magnitudes by the gravimetric sensor near the first aircraft contaminant collector and near second aircraft contaminant collector; or (v) the previously measured signal magnitude by the gravimetric sensor near the first aircraft contaminant collector; or (vi) the previously measured signal magnitude by the gravimetric sensor near the second aircraft contaminant collector is lower than the lower threshold, to the next predetermined higher sensitivity level, to maintain the signal magnitude at between the lower threshold and the upper threshold; and the first sample flow rate and/or the first sample flow duration is decreased when the measured signal magnitude of either (vii) the average of the previously measured signal magnitudes by the sensors near the first aircraft contaminant collector and near the second aircraft contaminant collector; or (viii) the previously measured signal magnitude by the gravimetric sensor near the first aircraft contaminant collector; or (ix) the previously measured signal magnitude by the gravimetric sensor near the second aircraft contaminant collector is higher than the than the upper threshold, to the next pre-determined lower sensitivity level, to maintain the signal magnitude to maintain the signal magnitude between the upper threshold and the lower threshold.

In accordance with embodiments of the method, the air contaminants comprise aerosols and/or particulates, and/or vapor(s).

In another embodiment, an aircraft air contaminant analyzer is provided comprising (a) at least one aircraft air contaminant collector comprising (i) a microporous medium comprising microporous flow-through channels and a chemoselective coating, wherein the microporous medium remains functional and desorbs captured air contaminants while being heated for a controlled time period, the at least one aircraft contaminant collector providing a first sample flow path, wherein the microporous medium is arranged across the first sample flow path; (ii) a thin film resistive heater, capable of heating to a temperature that vaporizes captured air contaminants, wherein the heater is in contact with the microporous medium; (b) a bypass section, comprising a bypass channel, the bypass channel including a second sample flow path, the bypass channel bypassing the at least one aircraft air contaminant collector; (c) a first substrate, having a top surface and a bottom surface; wherein the at least one contaminant collector is associated with the first substrate, the microporous medium and heater being thermally insulated from the first substrate; (d) a gravimetric sensor arranged to generate a proportionate resonant frequency response when air contaminant mass is added to or removed from the gravimetric sensor, for classifying air contaminant type; (e) a second substrate, having a top surface and a bottom surface; wherein the gravimetric sensor is associated with the top surface of the second substrate, the gravimetric sensor being separated from the contaminant collector by a constant distance, the gravimetric sensor being arranged to receive air contaminants desorbed from the membrane when the membrane is heated; (f) a support comprising a top surface and a bottom surface, the support comprising a common inlet port passing through the top surface and the bottom surface of the support, wherein the bottom surface of the second substrate is associated with the top surface of the support; the aircraft air contaminant analyzer further comprising an aircraft air contaminant inlet port; a flow-through heater block; and a first valve, arranged upstream of the common inlet port; a second valve, downstream of the at least one aircraft air contaminant collector, and arranged along the first sample flow path; a third valve arranged along the second sample flow path; a pump arranged to generate flow along the first sample flow path and along the second sample flow path; a pressure sensor arranged between the first valve, the second valve, and the third valve; and a temperature sensor arranged to measure temperature in the flow-through heater block; (h) a resonant frequency measurement device, arranged to measure the proportionate resonant frequency response generated by the gravimetric sensor as the air contaminant is added to and removed from the gravimetric sensor; (i) a computer readable medium bearing an air contaminant recognition program and calibration data; and (j) a processor configured: to execute the air contaminant recognition program, the contaminant recognition program including a module configured to classify the air contaminant by type, and to measure response signal magnitudes from the proportionate resonant frequency response generated by the gravimetric sensor, and a module programmed to use the calibration data for comparison with the signal magnitude to calculate air contaminant concentration; and, to execute a sensitivity control program, the sensitivity control program including a module configured to maintain the signal magnitude at a predetermined target level or within a predetermined upper threshold and a predetermined lower threshold, by controlling the first valve, the second valve, and/or the third valve and/or the pump to: increase the first sample flow rates and/or the first sample flow durations when the signal magnitude is less than the predetermined target level or the predetermined lower threshold; decrease the first sample flow rates and/or the first sample flow durations when the proportionate resonant frequency response is greater than the predetermined target level or the predetermined upper threshold.

In some embodiments, the aircraft air contaminant analyzer further comprises an additional aircraft air contaminant collector such that the analyzer comprises a first aircraft air contaminant collector and a second aircraft air contaminant collector; the first sample flow path including a first sample portion flow path and a second sample portion flow path; wherein the first aircraft air contaminant collector is arranged along the first sample portion flow path, the aircraft air contaminant analyzer including a first adjustable flow controller communicating with the first sample portion flow path; and the second aircraft air contaminant collector is arranged along the second sample portion flow path, the aircraft air contaminant analyzer including a second adjustable flow controller communicating with the second sample portion flow path; wherein the aircraft air contaminant analyzer includes the second valve arranged downstream of the first sample portion flow path and the second sample portion flow path; and, wherein the bypass section providing the second sample flow path bypasses the first aircraft air contaminant collector and the first sample portion flow path, and bypasses the second aircraft air contaminant collector and the second sample portion flow path and wherein the third valve is arranged downstream of the second sample flow path; the first aircraft air contaminant collector and the second aircraft air contaminant collector each separately comprising (i) a microporous medium comprising microporous flow through channels arranged across the sample portion flow path, the microporous medium having a chemoselective coating; and, (ii) a thin film resistive heater, capable of heating to a temperature that vaporizes captured air contaminants, wherein the heater is in contact with the microporous medium; the aircraft air contaminant analyzer also including a gravimetric sensor arranged near each respective microporous medium to generate a proportionate resonant frequency response when air contaminant mass is added to or removed from the respective gravimetric sensor, for classifying air contaminant type; the pump generating flow along the first sample portion flow path, the second sample portion flow path, and along the second sample flow path; wherein the air contaminant recognition program includes a module configured to measure response signal magnitudes from the proportionate resonant frequency responses generated by the gravimetric sensors near each respective collector, and a module to calculate air contaminant concentrations using one or both signal magnitudes, wherein the sensitivity control program includes a module configured to maintain either an average of the previously measured signal magnitudes by the gravimetric sensors near the first aircraft contaminant collector and near the second aircraft contaminant collector; or the previously measured signal magnitude of the gravimetric sensor near the first aircraft contaminant collector; or the previously measured signal magnitude of the gravimetric sensor near the second aircraft contaminant collector, at a predetermined target level or within a predetermined upper threshold and a predetermined lower threshold, by controlling the first valve, the second valve, and/or the third valve and/or the pump to: increase the first sample flow rates and/or the first sample flow durations when the signal magnitude is less than the predetermined target level or the predetermined lower threshold; decrease the first sample flow rates and/or the first sample flow durations when the signal magnitude is greater than the predetermined target level or the predetermined upper threshold.

In accordance with embodiments of the invention, two primary flow paths are utilized, one primary flow path passing through the aircraft air contaminant collector(s), and the other primary flow path bypassing the collectors. In those embodiments wherein the aircraft air contaminant analyzer includes two or more air contaminant collectors, the first primary flow path is split into separate sub-flow paths (first and second sample portion flow paths) passing through the separate air contaminant collectors, wherein the sub-flow paths are not controlled independently. Rather, in an embodiment including first and second air contaminant collectors, a one-time adjustment is used to redistribute the fraction of the first primary flow path's flow rate that goes through the first collector versus the fraction of the first primary flow path's flow rate that goes through the second collector, so that both collectors have similar signal magnitudes. The sub-paths merge before passing through a common downstream valve, so the flow rate through the common downstream valve is the sum of the first sample portion flow rate and second sample portion flow rate.

While repeatedly measuring the gravimetric sensor's response (or the gravimetric sensors' responses), each aircraft air contaminant collector's microporous medium is heated to vaporize the collected contaminants passed along the sub-flow path such that the vaporized contaminants are transferred to the gravimetric sensor to be measured. The measurement rate is sufficient to resolve the gravimetric sensor's/sensors' response/responses, which is in the shape of the sensor's frequency versus time curve as it absorbs and subsequently desorbs contaminants released from the microporous medium.

In accordance with one embodiment, flow rates and/or flow durations are adjusted such that the measured signal magnitude is maintained at a target level. In accordance with another embodiment, flow rates and/or flow durations are adjusted such that the measured signal magnitude is maintained between upper and lower target thresholds.

Advantageously, the sensitivity of an aerosol composition analyzer can be rapidly tuned to achieve both adequate sensitivity and reduced fouling over a range of contaminant concentrations and vapor pressures, while simultaneously providing rapid response and recovery times. Thus, for example, fouling can be reduced when the contaminant concentration is high and the sampling volume is low, and a rapid response can be provided even when contaminant concentration is low and the sampling volume is high, while maintaining sensitivity under both conditions. In another advantage, when multiple contaminants are present, some having different concentrations and vapor pressures than others, the analyzer can be rapidly tuned to detect the different contaminants.

Embodiments of the aircraft air contaminant analyzer according to the invention are not "single use," e.g., they are resistant to fouling and can be used to repeatedly measure the contaminant concentration(s) and determine the contaminant type(s).

In another advantage, particularly when two or more aircraft air contaminant collectors are utilized, different fluids with similar properties (e.g., vapor pressure and/or density) can be more accurately classified.

The contaminants determined and classified can comprise aerosols, particulates, and/or gases.

In a typical embodiment, an aircraft air contaminant analyzer can be located in the ECS (Environmental Control System) vent or duct since there will be a delay before the contaminant concentration in the large volume cabin increases to the level coming out of the ECS vents. However, a variety of locations are suitable for an analyzer, such as, e.g., in the cockpit, cabin, overhead luggage compartment, storage compartment, galley area, avionics bay, auxiliary power units, etc. Alternatively, an analyzer can be installed in one location and air from another location directed to the analyzer via a variety of air transfer devices including, e.g., piping, tubing, and/or ducts.

Alternatively, or additionally, an aircraft air contaminant analyzer can be located, e.g., at or near a bleed air line, wherein pressurized air from an engine is transferred to the ECS. One benefit of an analyzer at or near the bleed air line is that sampling bleed air from each engine informs and can identify which engine is faulty, allowing the crew to stop supplying contaminated bleed air from a faulty engine to the ECS. In contrast, an analyzer located in the cabin, whether sampling from the cabin or ECS vent or ECS duct will inform there is a contaminant source, but not which engine or APU (auxiliary power unit) is the source of contamination.

The analyzer includes a measurement circuit to measure frequency at a sufficient rate to precisely resolve the gravimetric sensor's response, typically about 10 to about 100 measurements per second per gravimetric sensor. Measurement is synchronized with other analyzer functions, particularly, the function of heating the microporous medium. Measurement is typically over a duration sufficient to resolve the maximum frequency change and the rate of recovery of the gravimetric sensor's response, typically, for example, a duration of about 1 second to about 4 seconds long.

A sufficient volume of sample at a prescribed rate (for example, about 500 to about 2000 standard cubic centimeter per minute (sccm)) for a prescribed period of time (for example, about 10 to about 60 seconds) is flowed through the analyzer to achieve a response magnitude sufficiently over the measurement noise level to resolve the shape of the sensor's frequency versus time curve, typically, a signal-to-noise ratio of about 4:1 or greater.

The kinetics of transfer, adsorption and desorption of the different contaminants results in different response shapes for the different contaminants. Illustratively, if 4 different compounds (e.g., nitromethane triacetone triperoxide, ethylene glycol dinitrate, and 2,3 dimethyl 2,3 dinitrobutane) were superimposed on a single graph for ease of reference, the shape of sensor frequency versus time responses for the compounds would show that the higher vapor pressure (lighter) compounds are released from the membrane more quickly than the lower vapor pressure (heavier) compounds, e.g., nitromethane is released before triacetone triperoxide, ethylene glycol dinitrate, and 2,3 dimethyl 2,3 dinitrobutane.

The flow along the sample flow path (or sub-flow path) through the microporous medium (generated by the pump) should be stopped such that it is zero or nearly zero (e.g., about 5 sccm or less) before the microporous medium is heated, e.g., typically, flow should be stopped for at least 0.2 seconds before heating.

Preferably, while repeatedly measuring frequency, the microporous medium is heated by applying a voltage step bringing it to a temperature of at least about 400° C. in about 0.1 seconds. Typically, the microporous medium is heated to at least about 200° C., more typically, at least about 400° C., in some embodiments, to about 550° C., for at least about 1 second, preferably, at least about 2 seconds (e.g., up to about 10 second, or more), to vaporize (desorb) the contaminant(s) so that the next measurement can begin from a "fresh start." In order to zero out ("self-zero") gravimetric sensor drift, the sensor's response is referenced to the frequency the sensor had just before heating the microporous medium.

When the microporous medium is not being heated, the analyzer is preferably maintained at a fixed temperature, e.g., a fixed temperature in the range of from about 30° C. to about 70° C.

The contaminant(s) can be classified by type using a pattern recognition algorithm to recognize each contaminant by its unique response, the shape of the sensor's frequency versus time curve, which is influenced by the contaminant's material properties such as, but not limited to, one or more of any of the following: vapor pressure, heat capacity, heat of condensation, heat of evaporation, absorption and desorption kinetics, and diffusion rate. A variety of algorithms can be used to classify the contaminant(s) from the contaminant-specific response shape. Suitable algorithms include, for example, neural nets, principal component analysis, support vector machine based classification, linear discriminant analysis and decision tree analysis.

Concentration of the contaminant(s) can be calculated by comparing the magnitude of the response(s) to a pre-determined calibration file, e.g., a curve or lookup table giving values for the contaminant concentration(s) as a function of the magnitude of the response(s).

The signal magnitude is above the sensor noise level for more accurate classification of the contaminant by type. Preferably, the signal magnitude is not so large that excess contaminant is collected as that may decrease sensor life.

In some embodiments, the signal magnitude is a frequency shift (e.g., a maximum frequency shift (MFS)) measured by the gravimetric sensor. For example, in some embodiments wherein the signal magnitude is an MFS, the target level is typically in the range of from about 100 Hz to about 1000 Hz, preferably in the range of from about 300 Hz to about 500 Hz.

In some other embodiments, the frequency shift is not an MFS, e.g., the frequency shift could be measured at some fixed time after the collector is energized, or a sum of frequencies at two or more times, or a sum (i.e., area under the curve) over the entire measurement or some portion of it.

The gravimetric sensor (which can comprise a single sensor or a sensor array) generates a precise and proportionate frequency response to mass added or removed from the sensor. Preferably, the response is provided over a wide dynamic range, such that it is not over-dampened by small quantities of transferred contaminant (analyte). The gravimetric sensor is operated as part of an amplified oscillator circuit to maintain it at resonance.

Each of the components of the invention will now be described in more detail below, wherein like components have like reference numbers.

Figure 2:
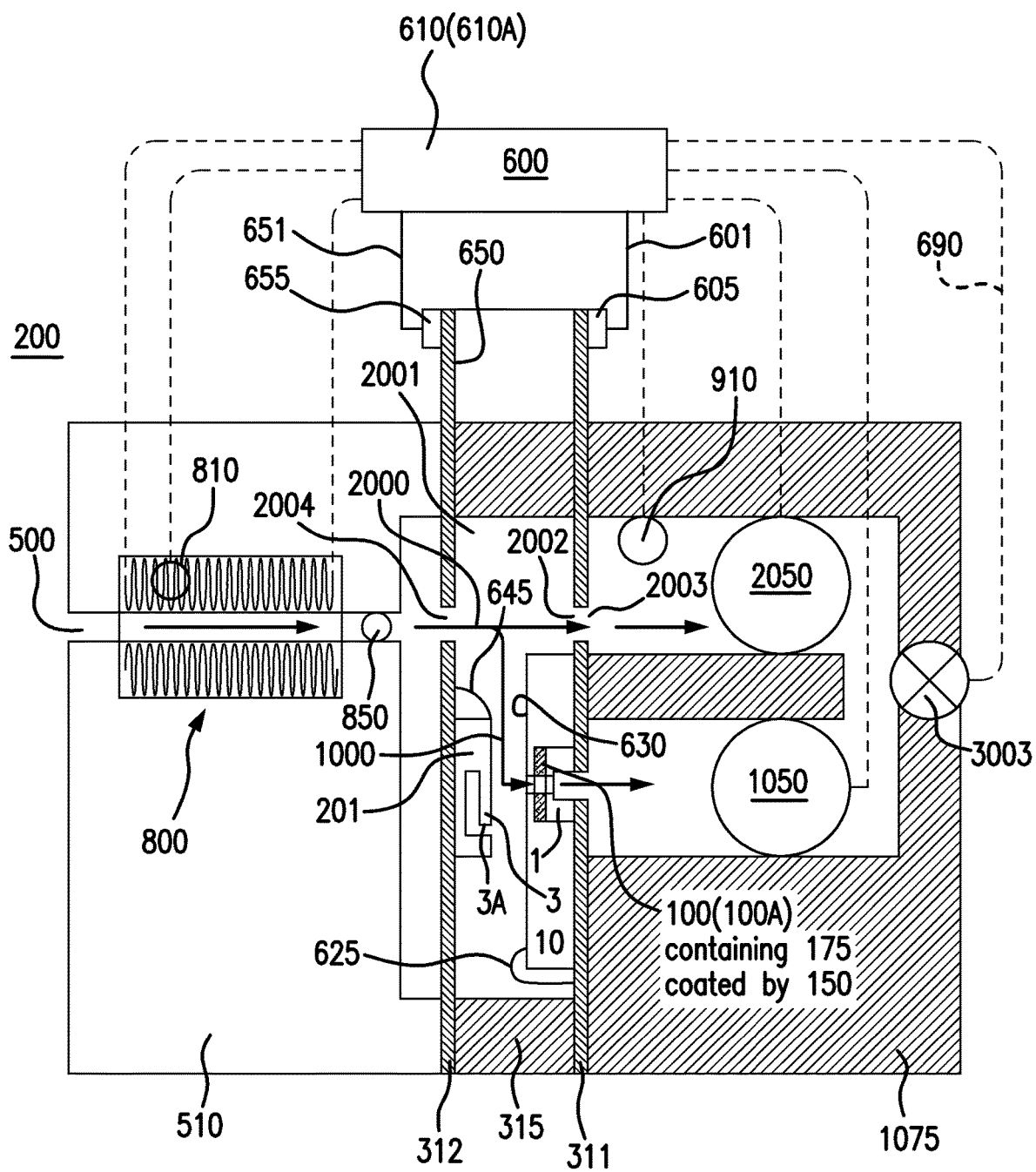

While embodiments of the invention can be carried out using one aircraft air collector, or two or more aircraft air collectors, FIG. 1 shows, illustratively, a diagrammatic top view of two aircraft air collectors 1, 1' of an illustrative air craft air contaminant analyzer according to an embodiment of the invention. FIG. 2 is a diagrammatic representation of the air craft air contaminant analyzer along line A-A of FIG. 1, and FIG. 3 is a diagrammatic representation of the air craft air contaminant analyzer along line B-B of FIG. 1.

Figure 3:
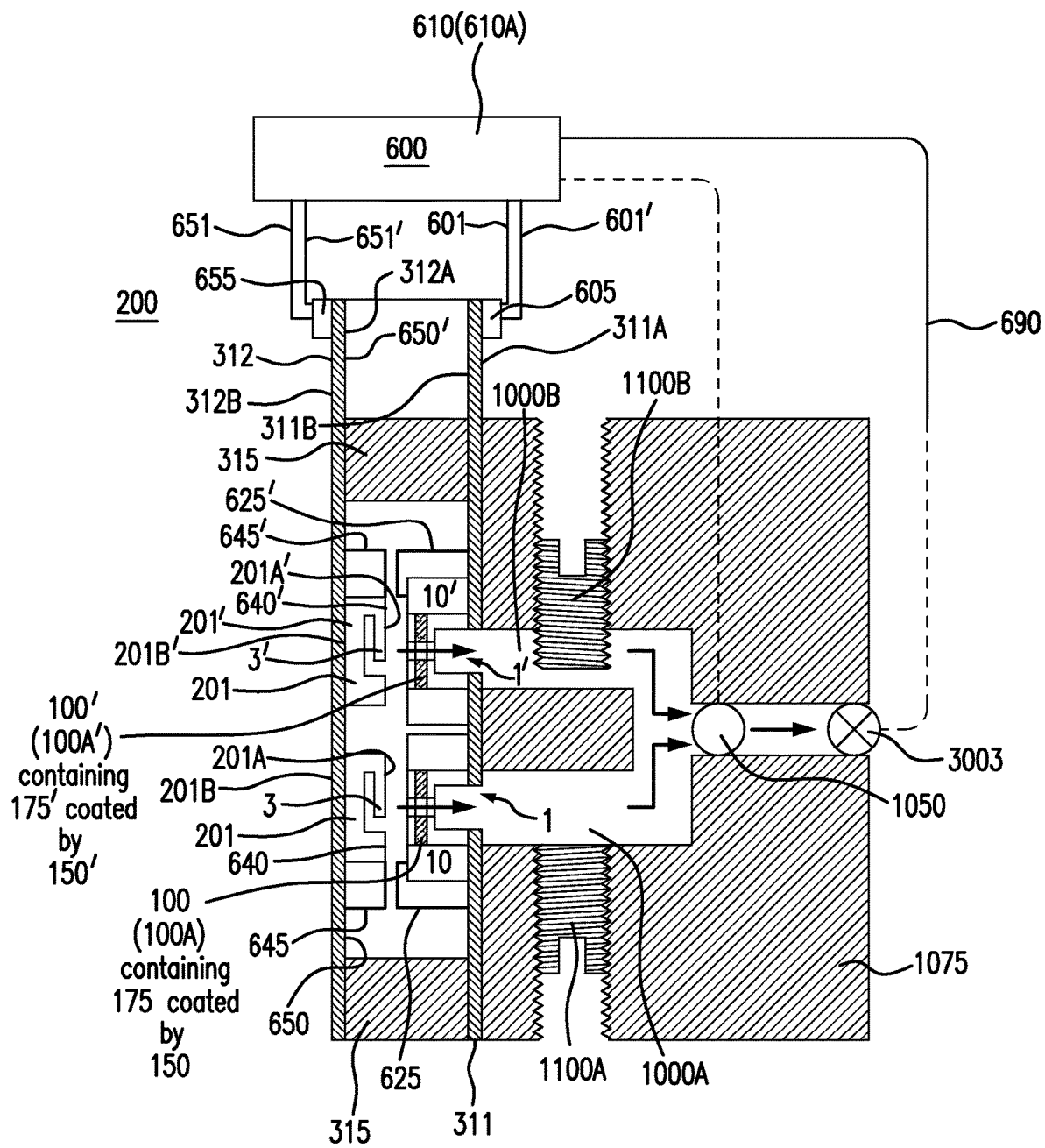

In the illustrative embodiment shown in FIGS. 2 and 3, an aircraft air contaminant analyzer 200 comprises an aircraft air contaminant analyzer inlet 500 for inlet flow of aircraft air (shown in FIG. 2, also showing an optional inlet manifold 510 including the aircraft air contaminant analyzer inlet 500), a flow-through heater 800 for heating the aircraft air, the heater including a temperature sensor 810; an electronically controllable first valve 850; a first aircraft air contaminant collector 1 and a second aircraft air contaminant collector 1'; providing a first sample portion flow path 1000A and a second sample portion flow path 1000B, respectively, the respective collectors.

Using FIGS. 4A-4D for reference, illustrating an aircraft air contaminant collector (since first aircraft air contaminant collector 1 and a second aircraft air contaminant collector 1' have the same components, FIGS. 2 and 3 list the components of second aircraft containment collector with a "'", e.g., 10', 1011', 100', etc.), first aircraft air contaminant collector 1 comprises a base 10, comprising a first substrate 1011, comprising a first substrate primary layer 101 having a first substrate top layer 101A and a first substrate bottom layer 101B (FIG. 4D), and a porous medium 100 (e.g., a microporous membrane 100A) on the first substrate, the porous medium having a top surface 111 and a bottom surface 112 (FIGS. 4C and 4D), the porous medium comprising microporous flow-through channels 115 (through the top surface and the bottom surface of the porous medium) and a chemoselective coating 150 (shown in FIGS. 4A, 4B, and 4D), wherein the porous medium remains functional and desorbs captured air contaminants while being heated for a controlled time period, and a thin film resistive heater 175, capable of heating to a temperature that vaporizes captured air contaminants, wherein the heater is in contact with (in and/or on) the top surface of the porous medium; wherein the layers 101A and 101B, the porous medium 100, the heater 175, wire traces 620 (that can communicate with wirebonds (not shown) communicating with the heater 175) and an optional packaging layer 699 (covering at least a portion of the wire traces, e.g., providing low resistance and allowing the wirebonds to form a reliable electrical contact and more efficiently move heater current from the wirebonds to the heater) are associated with (e.g., mounted to or fabricated on) the first substrate primary layer 101 by, for example, additive processes, and channels 115 and tethers 190 (discussed below), as well as the cavity below the porous medium 100 (shown in FIG. 4D) are fabricated by, for example, subtractive processes.

While FIGS. 4A-4D show a first substrate 101' comprising a first substrate primary layer 101 having a first substrate top layer 101A and a first substrate bottom layer 101B, it should be recognized by one of skill in the art that other processes for forming the porous medium 100 may not require layers 101A and/or 101B.

Figure 4A:
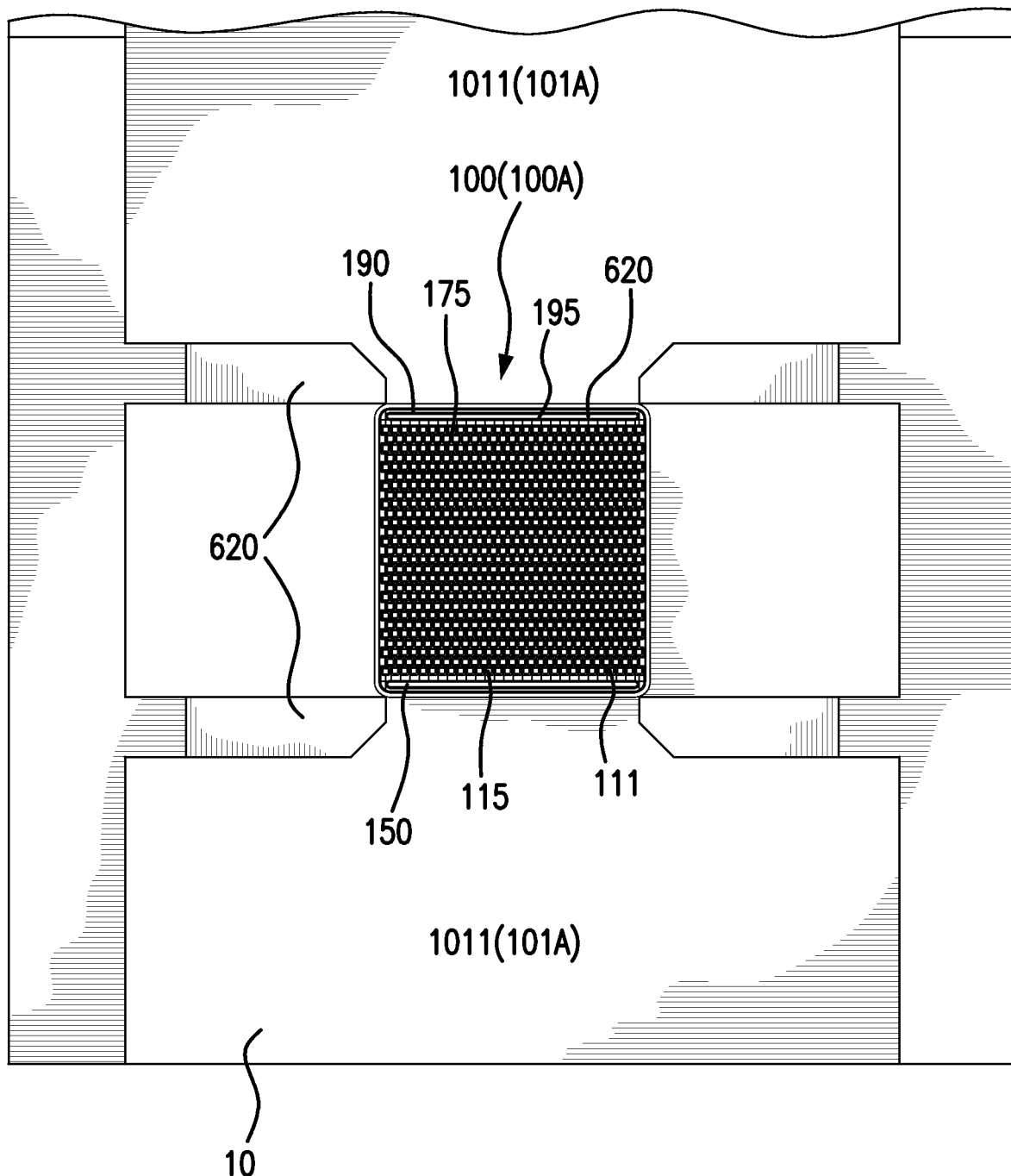
Figure 4B:
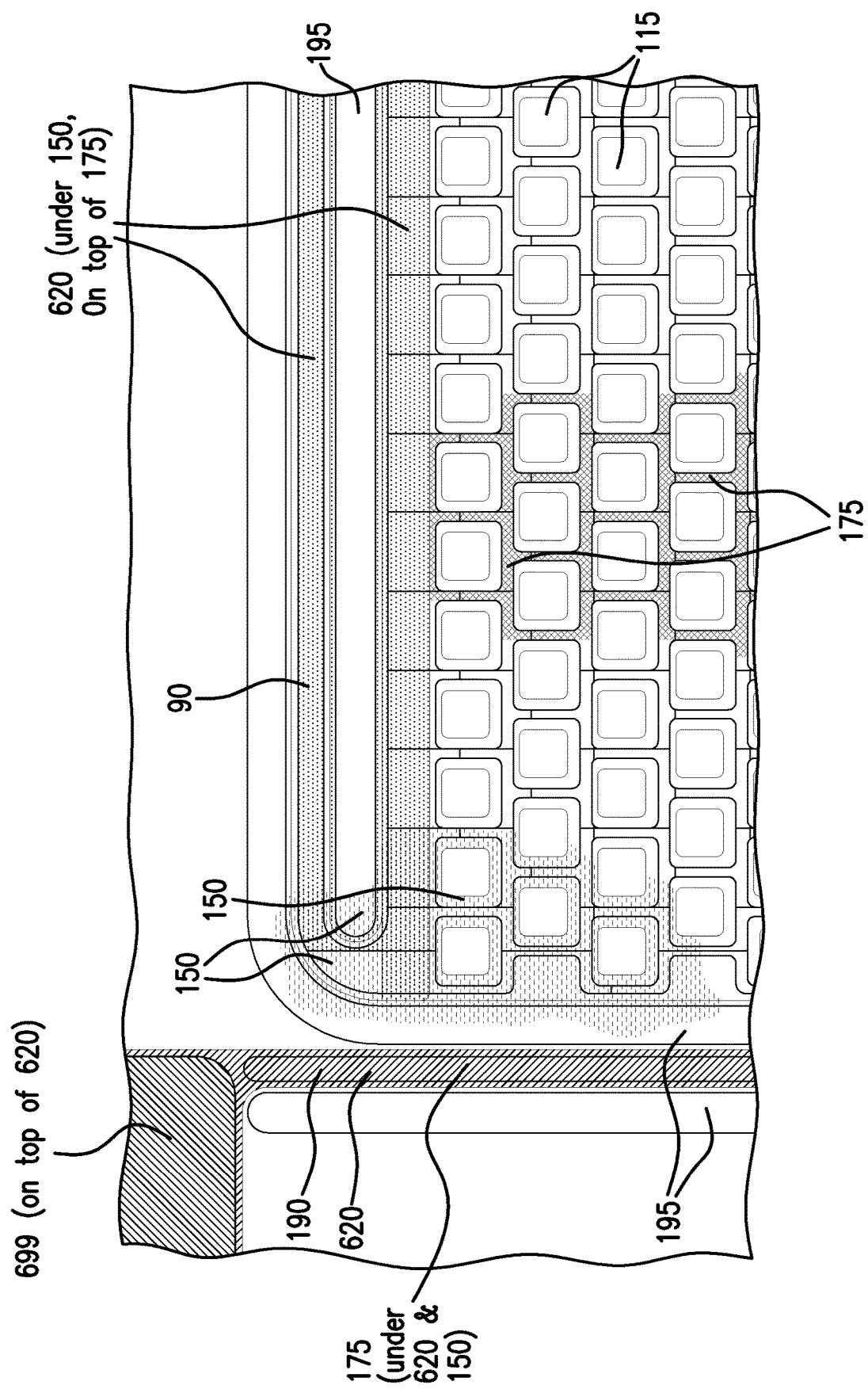
Figure 4C:
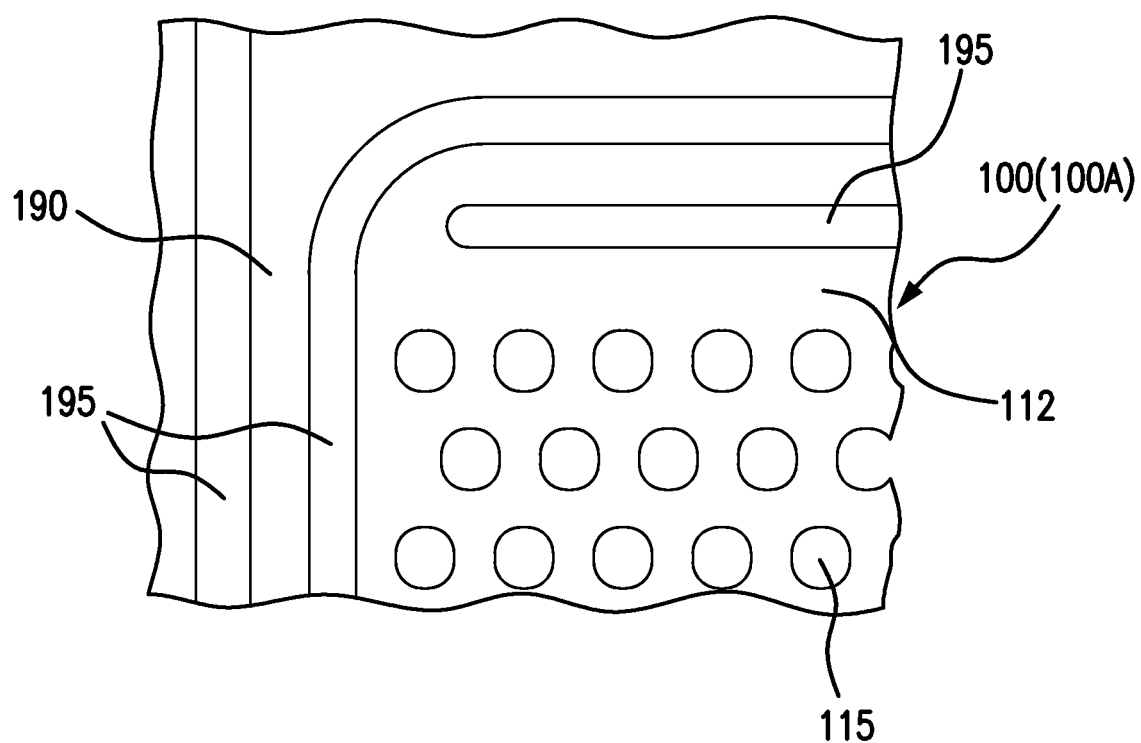

Typically, the chemoselective coating 150 covers all surfaces of the membrane (e.g., top, bottom, the flow-through channels; coating in channels/pores not shown in FIG. 4B) as well as the top of the heater and electrical traces, without covering the packaging layer 699.

Figure 4D:
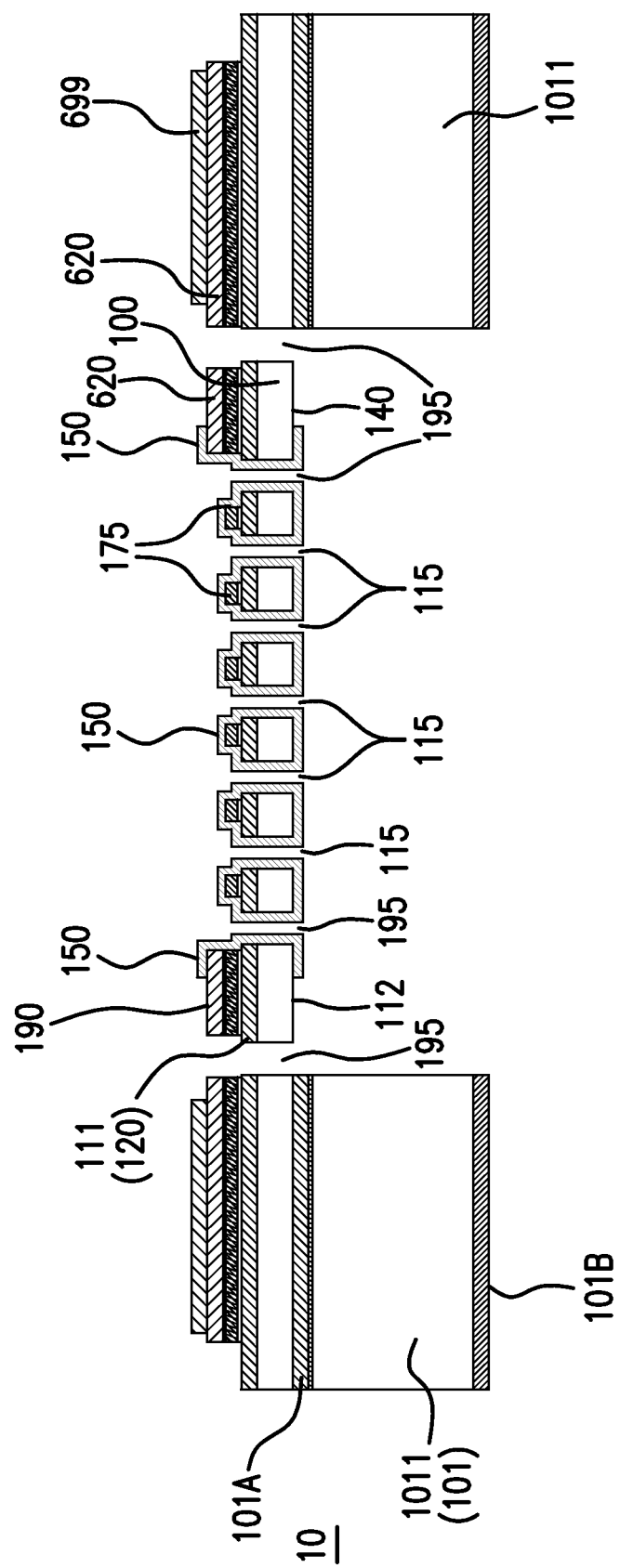

Preferably, the porous membrane and heater are thermally insulated from the base 10 and the first substrate 1011, for example, the porous member is thermally insulated from 101, 101A, and 101B (e.g., by tethers 190 connecting the porous member to the substrate, e.g., as shown in FIGS. 4A, 4B, and 4D) to reduce conductive heat loss at the edges of the porous member, also allowing rapid and uniform heating with low power. In an embodiment, channels 195 are etched through the first substrate, and define the tethers (e.g., the tethers are portions of the first substrate remaining after channels have been etched therethrough). In contrast with the flow-through channels 115 (typically having a diameter of about 50 micrometers or less), the channels 195 are typically elongated, and define the tethers.

In the embodiment illustrated in FIGS. 4B and 4D, the thin film resistive heater 175 is arranged in or on the top surface 111 of the porous membrane (surrounding the flow-through channels 115 of the porous membrane), and on the tethers.

In some embodiments, e.g., as illustrated diagrammatically in FIG. 4D, the top surface 111 of the porous member comprises an insulating layer 120 (e.g., $SiO_2$) underneath the heater (and any other structure carrying current, e.g., electrical traces) to prevent current from shorting through the porous membrane.

As shown in FIG. 3, the first sample portion flow path 1000A and the second sample portion flow path 1000B join downstream of the collectors 1, 1' in exit manifold 1075 before passing through an electronically controllable second valve 1050. FIG. 3 also shows first and second adjustable flow controllers 1100A and 1100B communicating with the respective first sample portion flow path 1000A and the second sample portion flow path 1000B. Typically, the controllers are adjusted at the time of calibration, and can be either manually adjusted or adjusted using powered activation, for example, using an electrically powered valve.

As shown in FIG. 2, the illustrated embodiment of the aircraft air contaminant analyzer also includes a bypass section 2001 providing a bypass sample flow path 2000, the bypass section comprising a bypass channel port 2002 and a bypass channel 2003, the bypass sample flow path passing through an electronically controllable third valve 2050. The bypass sample flow path bypasses the first sample portion flow path 1000A (and the second sample portion flow path 1000B, if present).

The valves 850, 1050, 2050 are used to control pressure during the sensing part of the detection cycle. FIG. 2 also shows a pressure sensor 910 for sensing pressure such that electronics control the operation of the valves (e.g., the valves are closed in the correct order when a desired pressure is reached). Preferably, during sensing, valve 850 is closed first, and the valves 1050 and 2050 are closed when a desired pressure (less than the cabin pressure, which is typically about 10 psia) is reached.

Typically, the flow-through heater 800 controls the temperature of the incoming aircraft air at a fixed temperature in the range of from about 30° C. to about 70° C., wherein the temperature sensor 810 senses the temperature such that electronics controls the operation of the heater to maintain the fixed temperature.

In these illustrated embodiments, the aircraft air contaminant collectors 1, 1' are associated with (e.g., mounted on) a first support 311, typically a printed circuit board, the first support having a top surface 311A and a bottom surface 311B. As will be discussed in more detail below, the first sample portion flow path and the second sample portion flow path pass through separate portions of the first support, and flow through exit manifold 1075. Flow along the first sample portion flow path, the second sample portion flow path, and the bypass sample flow path is generated by a pump 3003.

The analyzer 200 includes gravimetric sensors 3, 3' arranged near each collector along the first and second sample portion flow paths to generate a proportionate resonant frequency responses when air contaminant mass is added to or removed from the gravimetric sensors, for classifying air contaminant type; and second substrates 201, 201' each having a top surface 201A, 201A' and a bottom surface 201B, 201B'; wherein the gravimetric sensors 3, 3' is associated with (e.g., mounted on or fabricated within, e.g., by subtractive and additive processes) the top surfaces of the second substrates, the gravimetric sensors being separated from the contaminant collectors by a constant distance, the gravimetric sensors being arranged to receive air contaminants desorbed from the respective microporous medium when the microporous medium is heated.

The embodiment of the analyzer shown in FIGS. 2 and 3 (some components are only labeled on FIG. 2 or only labeled on FIG. 3) also include a second support 312 comprising a top surface 312A and a bottom surface 312B, the second support comprising a common inlet 2004 for inlet flow of aircraft air passing through the top surface and the bottom surface of the support, wherein the bottom surface of the second substrate is associated with (e.g., mounted on) the top surface of the second support. Typically, the second support comprises a printed circuit board. Preferably, as shown in FIG. 2, the common inlet 2004 is aligned with bypass channel port 2002, e.g., to allow large particles to pass through the bypass channel port easily.

Separation between the gravimetric sensor and the microporous medium should be kept constant, typically at a distance of about 0.1 mm to about 2 mm, preferably about 0.4 mm to about 0.4 mm. For example, FIGS. 2 and 3 show spacers 315 between the first support 311 and the second support 312 for maintaining the spacing between the sensor and the microporous medium. Preferably, the length of the spacers is such that the separation between the collector and the gravimetric sensor facing surfaces are about 0.2 mm to about 0.4 mm.

The embodiment shown in FIGS. 2 and 3 also include electronics 600, comprising a power source or a connection to a power source, a power regulator, a measurement circuit 610 comprising a resonant frequency measurement device 610A comprising an oscillator and a field-programmable gate array (FPGA), arranged to measure the proportionate resonant frequency response generated by the resonator array to allow classification of air contaminant type(s); a computer readable medium bearing an air contaminant recognition program; a processor configured to execute the air contaminant recognition program, the contaminant recognition program including a module configured to measure oscillation rate and classify air contaminant type(s), and programmed with a calibration table for comparison with magnitudes of the proportionate resonant frequency responses generated by the resonator array(s) to calculate air contaminant concentration(s) and determine air contaminant type(s). The air contaminant recognition program can also include a sensitivity control program, the sensitivity control program including a module configured to maintain the signal magnitude at a predetermined target level or within predetermined upper and lower thresholds, by controlling the valves and/or pump to: (a) increase the first sample flow rates and/or first sample flow durations when the signal magnitude is less than the predetermined target level or lower threshold; and (b) decrease the first sample flow rates and/or first sample flow durations when the proportionate resonant frequency response is greater than the predetermined target level or upper threshold. If desired, the air contaminant recognition program executed by the processor is stored upon a non-transitory computer-readable medium, and the processor displays (outputs) a value for the determined air contaminant type(s). For example, the value(s) can be displayed through a GUI using a display device (such as a hand-held device) operably arranged with the processor. Alternatively, or additionally, for example, the value(s) can be displayed by an illuminated indicator or communicated audibly.

Figure 5:
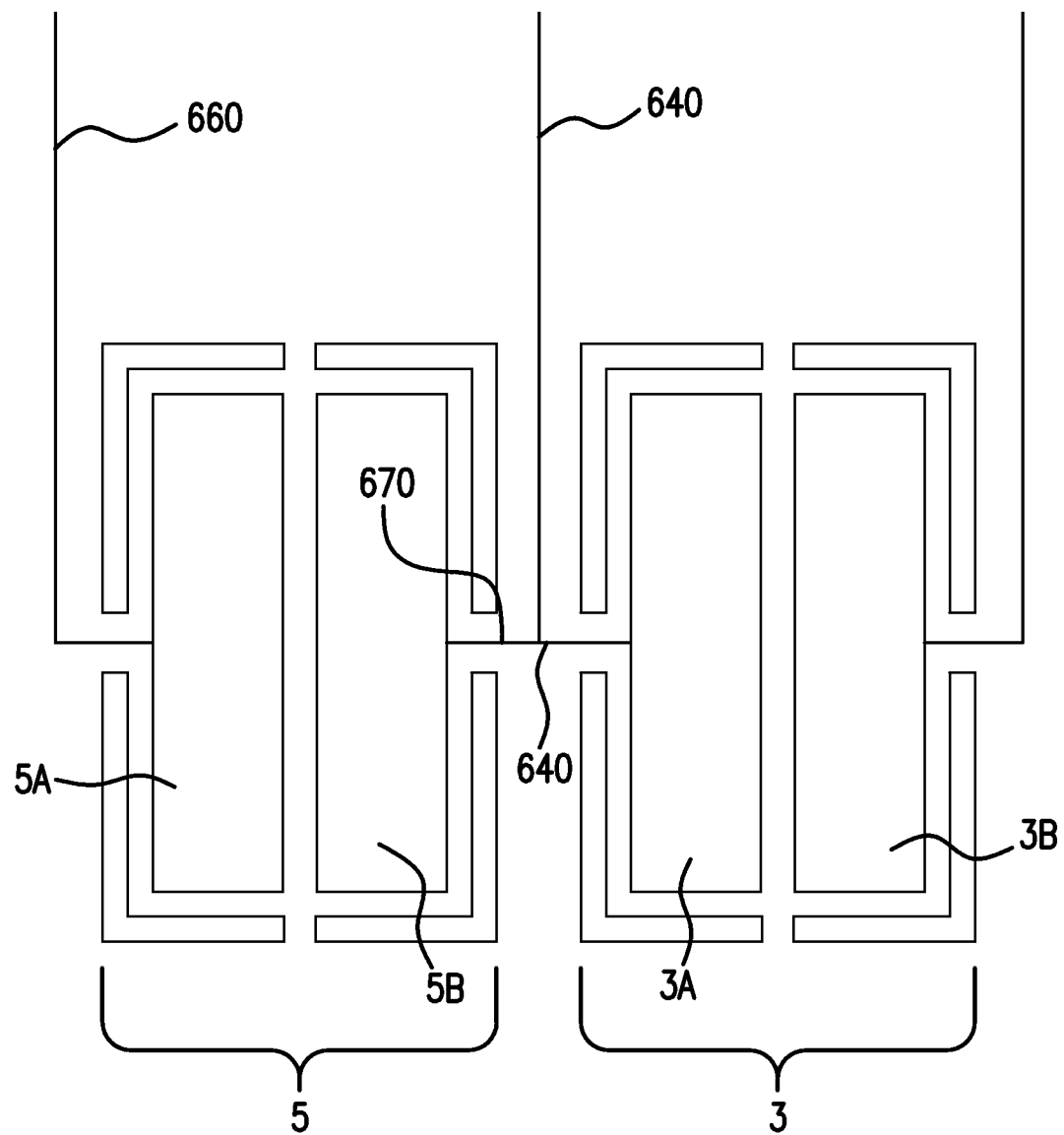
FIG. 5 is a diagrammatic representation showing an illustrative gravimetric sensor (having first and second electrodes), the sensor also including a balance capacitor (having first and second balance capacitor electrodes) as part of an aircraft air contaminant analyzer according to an embodiment of the invention.

The electronics can have a variety of arrangements as known in the art. In the illustrated embodiment shown in FIGS. 2 and 3, the electronics provide power when needed to the respective heater 175, 175' via a cable 601, 601', connector 605, 605', electrical traces 620, 620' fabricated into first support 311 (so traces not visible), wirebonds 625, 625', and traces 630, 630' fabricated onto collector 10 (so traces not visible), and power to the pump 3003 (discussed below) when needed via cable 690. As discussed below with respect to FIGS. 2 and 3, the electronics with respect to the gravimetric sensors can also include, for example, electrical trace 640, 640', wirebonds 645, 645', electrical traces 650, 650' fabricated into second support 312 (so traces 650, 650' not visible), 660, 670 (as shown in FIG. 5), connector 655, and cable 651, 651'.

In those embodiments including additional collectors and gravimetric sensors, each gravimetric sensor would typically have its own oscillator circuit, electrical traces and wirebonds. They may have separate cables and connectors, or signals may be routed into multi-wire cables and connectors. One field programmable gate array (FPGA) is typically capable of counting the resonant frequencies of multiple gravimetric sensors. All collectors can be wired in parallel and heated from the same electronics power circuit, or alternately can be powered by separate circuits and heated independently, for example to different temperatures or durations.

If desired, resonance frequency can be measured using, for example, a phase lock loop or a digital signal processor (DSP) chip to perform frequency sweeps to identify the resonant frequency from the sweep spectra.

Alternatively, if desired, a resonant frequency measurement device comprising a laser and a photodetector can be arranged to measure the proportionate resonant frequency response generated by the gravimetric sensor.

A variety of pumps are suitable for use in accordance with embodiments of the invention. As shown in FIGS. 2 and 3, the pump 3003 is preferably positioned downstream of the one or more microporous media and the one or more gravimetric sensors, wherein optional inlet manifold 510, second support 312, first support 311, and spacer 315 isolate the sample to avoid its contamination or dilution, and to ensure that flow generated by the pump all flows through 100, 100', and the pump is positioned after the gravimetric sensors and the microporous media to ensure that the pump does not contaminate the sample, and the gravimetric sensors are positioned upstream of the microporous media with sample flow arranged to avoid flow toward the respective sensor surfaces, thus minimizing the transfer of contaminants and undesirable material (such as dust, aerosols, and/or particulates) onto the surfaces of the sensors.

In those embodiments including two or more aircraft air contaminant collectors and corresponding gravimetric sensors (providing a collector-sensor set), each collector-sensor set is maintained at the same environmental conditions (e.g., temperature, pressure, relative humidity) as the other set(s), as this provides better detection performance by reducing "noise" in the response patterns caused by measuring each set at different times or under different conditions. Preferably, all of the collector-sensor sets are arranged in close proximity.

Each collector-sensor set should have similar sensitivity as the other set(s) such that each provides responses above the noise level to provide good accuracy.

A variety of gravimetric sensors are suitable for use in embodiments of the invention, including, for example, gravimetric sensors selected from a thin film resonator (TFR), a surface acoustic wave (SAW) resonator, a thickness sheer mode (TSM) resonator (quartz crystal microbalance (QCM) resonator), an acoustic plate mode (APM) resonator, a flexural plate wave (FPW) resonator, a bulk acoustic wave (BAW) resonator, a piezoelectric bimorph resonator array sensor, and a tuning fork sensor.

In an embodiment, the sensor can be coated with functionalized $SiO_2$ nanoparticles (e.g., functionalized with tri-ethyoxysilanes) Suitable tri-ethyoxysilanes for producing functionalized $SiO_2$ nanoparticles include, for example, 3-[2-(3-Triethoxysilylpropoxy)ethoxy] sulfonlane, 95%; Phenethyltrimethoxysilane, tech-95; 3-Methyoxypropyltrimethoxysilane; N-(Acetylglycl)-3-Aminopropyltrimethoxysilane, 5% in methanol; and Dodecafluorodec-9-Ene-1-Yltrimethoxysilane, 95%. In some embodiments, the functionalized $SiO_2$ nanoparticles form self-assembled monolayers that can be deposited on the surface of the sensor.

In one embodiment, the gravimetric sensor comprises a piezoelectric bimorph resonator array comprising two active layers, the layers bending under resonance, the resonator array generating a proportionate change in resonant frequency upon the addition or removal of air contaminant mass. One example of such a gravimetric sensor is disclosed in U.S. Pat. No. 6,953,977.

In an embodiment shown in FIG. 5, the gravimetric sensor 3 includes a first electrode 3A (see also, FIG. 2) and a second electrode 3B (collectively forming a resonator) so that motion of the sensor is transduced into an electrical signal via the first electrode on the surface of the sensor, and the signal can be amplified and returned to the second electrode on the sensor surface to drive the sensor at resonance. The gravimetric sensor can further comprise an optional balance capacitor 5 comprising a first balance capacitor electrode 5A and a second balance capacitor electrode (measuring electrode) 5B included adjacent to the resonator to reduce the contributions of parasitic capacitances and resistances from the electrical signal, wherein the balance capacitor has similar or identical materials of construction and dimensions as the gravimetric sensor but is made incapable of motion (e.g., wherein there is no space on the substrate allowing the balance capacitor to move). The balance capacitor can be driven with, for example, a 180° phase shifted signal through a dedicated electrical trace to the first balance capacitor electrode. The signal transduced from the second balance capacitor electrode (measuring electrode) is combined with the signal transduced by the sensor's first electrode as it is routed to the electronics, e.g., a field programmable gate array (FPGA) and firmware that counts the rate of oscillation.

As recognized in the art, a variety of types of electronics are suitable for measuring the proportional frequency responses of the various gravimetric sensors.

A variety of materials are suitable for microporous media (e.g., microporous membranes) for use in accordance with embodiments of the invention. In addition to microporous membranes, suitable microporous media include fibrous materials, ceramics, printed structures, and micromachined structures. The microporous medium can be supported or unsupported. Typically, in those embodiments wherein the microporous medium is a microporous membrane, the membrane has a thickness in the range of at least about 20 micrometers to about 500 micrometers, more typically, a thickness in the range of about 50 micrometers to about 200 micrometers, though membranes can have lesser or greater thicknesses for some applications.

The microporous medium, e.g., the microporous membrane, is porous or perforated, providing suitable regular and/or irregular flow through channels and/or pores, e.g., about 5 micrometers to about 50 micrometers, typically, a 10 micrometers to about 30 micrometers, in size and/or diameter, though the pores or perforations can be smaller or larger for some applications. The membrane includes a chemoselective coating associated with (e.g., affixed and/or covalently bonded to) the top and bottom surfaces and the inside of the flow channels and/or pores and/or chemoselective particles in the bulk of the membrane.

A variety of chemoselective coatings are suitable for use in embodiments of the invention, e.g., porous silica, activated carbon, metal-organic frameworks (MOFs), zeolitic imidazolate frameworks (ZIFs), titania ($TiO_2$) particles, and zeolites, including hydrophobic zeolites and hydrophilic zeolites. Suitable zeolite coatings include, but are not limited to, Z100 (hydrophobic zeolite); Z110 (hydrophobic zeolite); Z300 (less hydrophobic zeolite); and Z810 (hydrophilic zeolite) (Zeochem LLC, Louisville, Ky.).

Suitable heaters, preferably, thin film resistive heaters, are known in the art. Illustrative heaters include, for example, platinum (Pt) and tantalum-platinum (TaPt) high temperature compatible thin film resistive heaters, which allow the microporous medium to be ohmically heated to, for example, about 550° C. without degradation. Preferably, the heater is fabricated in place onto the substrate, e.g., with a combination of deposition, lithography, and dissolution, processes.

A variety of heaters, temperature sensors, pressure sensors, valves, and adjustable flow controllers, are known in the art. While the adjustable flow controllers 1100A and 1100B are shown in FIG. 3 as threaded components that can be turned to project into the respective sample portion flow paths as desired, other types of adjustable flow controllers are known in the art, such as needle valves, ball valves, and constricted (squeezed) tubes.

A variety of materials are suitable for use as the first and second supports, the collector die, and the substrates, and suitable materials are known in the art and are readily manufacturable using microelectronics fabrication processes. For example, they can be fabricated from materials such as silicon. Typically, the materials are micromachinable, as they desirably allow micromachining to include, if desired, electrical structures such as traces, electrodes, and interconnects to bring electrical power where needed, and/or include mechanical structures such as suspended plates, tethers and membranes, and fluidic structures such as flow channels.

The following examples further illustrate the invention but, of course, should not be construed as in any way limiting its scope.

Example 1

This example demonstrates that signal magnitude (the change in frequency measured by the gravimetric sensor) changes as flow rate through the collector increases.

An aircraft air contaminant analyzer is set up as generally shown in FIGS. 1-3, with a resonator and balance capacitor set up as generally shown in FIG. 5.

The gravimetric sensor is a micromachined (MEMS) piezoelectric bimorph SiC—AlN resonator array with a wide mass-loading dynamic range and linear mass-loading response. The resonator has a small tethered plate that provide resonance modes with high mass-loading sensitivities, and includes thin film electrodes deposited onto the surface to electrically drive it to resonance and to transduce the motion back into an electrical signal for readout. The sensor includes metal traces to bring the signals to and from the resonator. The resonant frequencies are in the range of ~1 MHz to 30 MHz.

The balance capacitor is identical to the gravimetric sensor, but is arranged to be incapable of motion.

The aircraft air contaminant collector includes a microporous silicon membrane having about 25 micrometer diameter flow-through channels, the membrane further having a hydrophobic zeolite powder (Z300; Zeochem LLC, Louisville, Ky.) coating on the upstream, downstream, and flow-through channel surfaces.

The heater is a tantalum-platinum (TaPt) high temperature compatible thin film resistive heater, fabricated into the substrate and deposited directly on the membrane by processes known in the art.

Three contaminants, deicing fluid, turbine engine oil (AEROSHELL 560; Shell), and hydraulic fluid (Exxon HYJET; Exxon), each at a fixed concentration, are passed along the first sample flow path through the collector wherein the flow along the second sample flow path bypassing the collector is kept constant at 1.0 standard liter per minute (SLM). The flow duration is a constant for all measurements.

Figure 6:
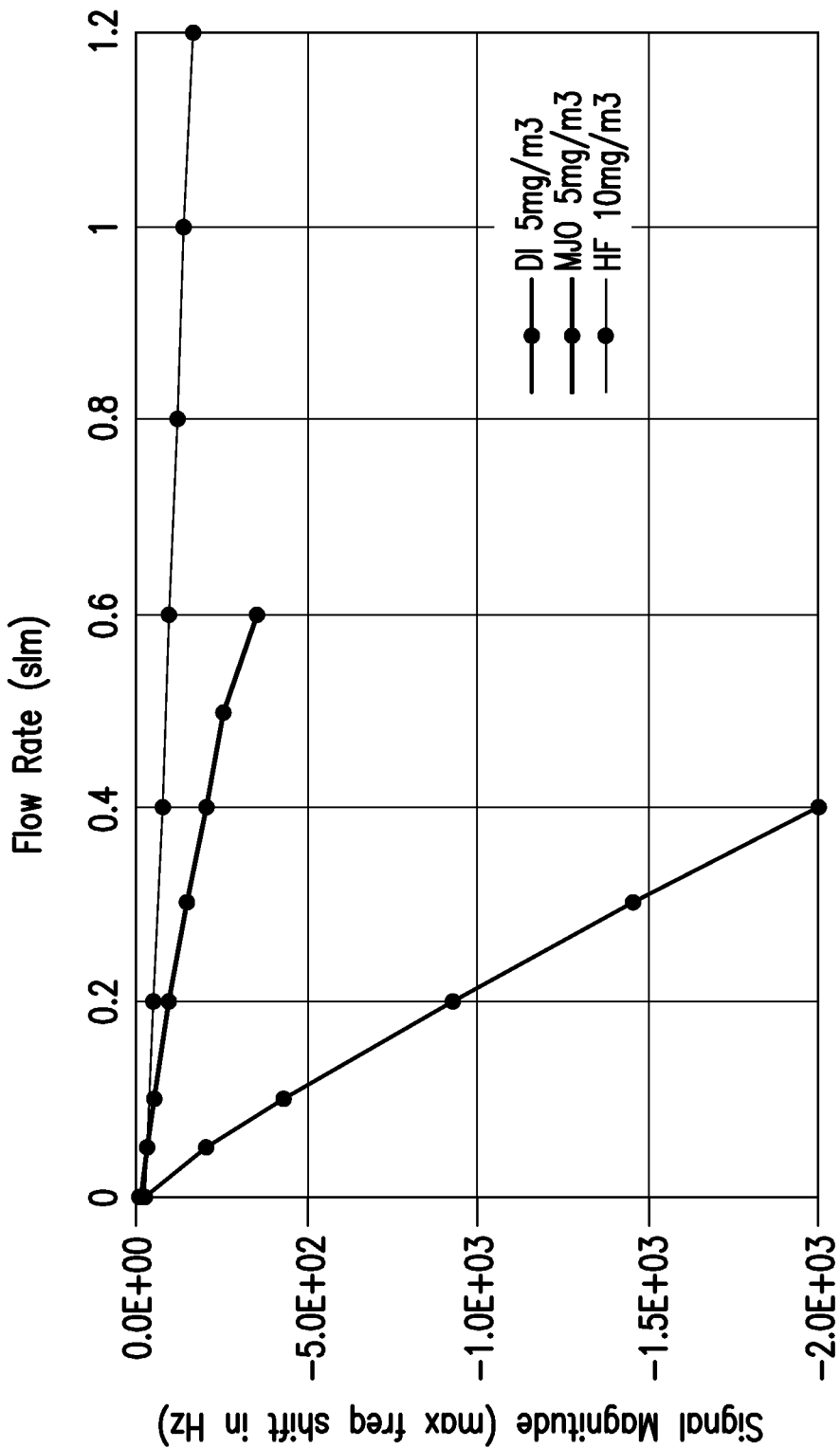
FIG. 6 shows the signal magnitude versus flow rate (at standard liter per minute (SLM)) along the first sample flow path through the collector for deicing fluid, turbine engine oil, and hydraulic fluid, each at a fixed concentration, wherein the flow along the second sample flow path bypassing the collector is kept constant at 1.0 SLM.

As shown in FIG. 6, higher flow rates along the first sample flow path correspond to more negative signal magnitudes (corresponding to more contaminant being detected), thereby demonstrating how modulating sample flow rate (and thus, sample volume) can be used to change the sensitivity of the aircraft air contaminant analyzer.

Example 2

This example demonstrates that an embodiment of the aircraft air contaminant analyzer functions over a range of concentrations.

An aircraft air contaminant analyzer is set up as generally described in Example 1.

The aircraft air contaminant analyzer is challenged with clean air, followed by challenges with three different concentrations of turbine engine oil (AEROSHELL 560; Shell), wherein the sampling time and flow rate through the collector are set prior to each challenge, to adjust the sensitivity so that the signal magnitudes of all three challenges are approximately equal.

The bypass flow rate is 1.0 SLM.

Figure 7:
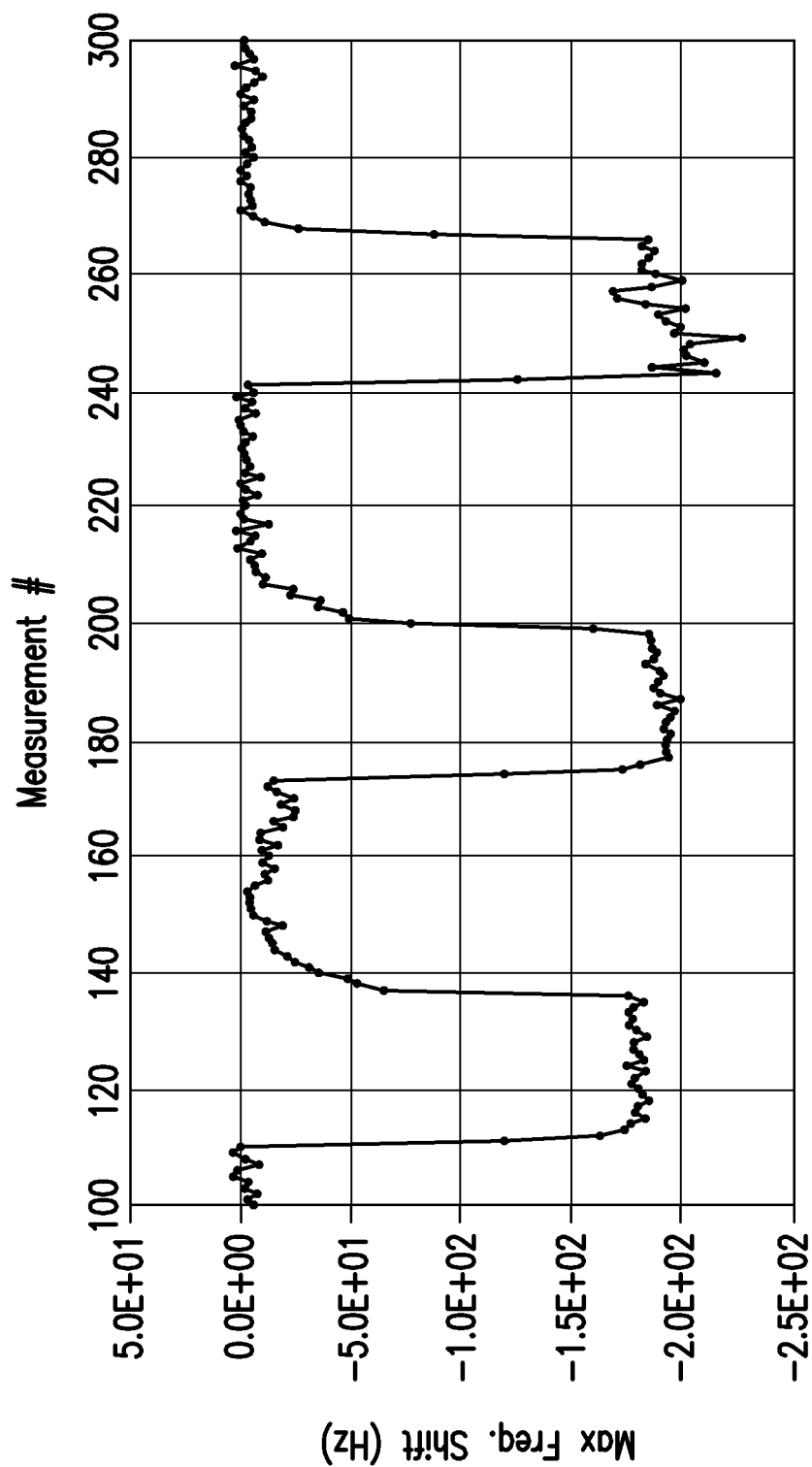
FIG. 7 shows, as a composite graph, a sequence of measurements as the aircraft air contaminant analyzer is challenged with three different concentrations of turbine engine oil, wherein the sampling time and flow rate through the collector are set prior to each challenge, so that the signal magnitudes of all three challenges are approximately equal.

FIG. 7 shows, as a composite graph, the sequence of measurements of turbine engine oil after the aircraft air contaminant analyzer is challenged with clean air before challenges with the engine oil, wherein measurements 110-137 are at a concentration of 5 mg/m$^3$, 11 seconds sample time, 300 standard cubic centimeter per minute (sccm) flow rate; measurements 175-199 are at a concentration of 0.5 mg/m$^3$, 16.5 seconds sample time, 1200 sccm flow rate; and measurements 242-265 are at a concentration of 50 mg/m$^3$, 11 seconds sample time, 18.5 sccm flow rate.

The data in FIG. 7 show that sample time and/or flow rate can be used to sensitize and desensitize an embodiment of the aircraft air contaminant analyzer, allowing it to function over a range of concentrations.

Example 3

In this Example, an aircraft contaminant analyzer is arranged without a bypass, wherein a pair of gravimetric sensors measures the desorption from a collector comprising a membrane coated with a hydrophobic zeolite coating (Z300; Zeochem LLC, Louisville, Ky.).

Figure 8:
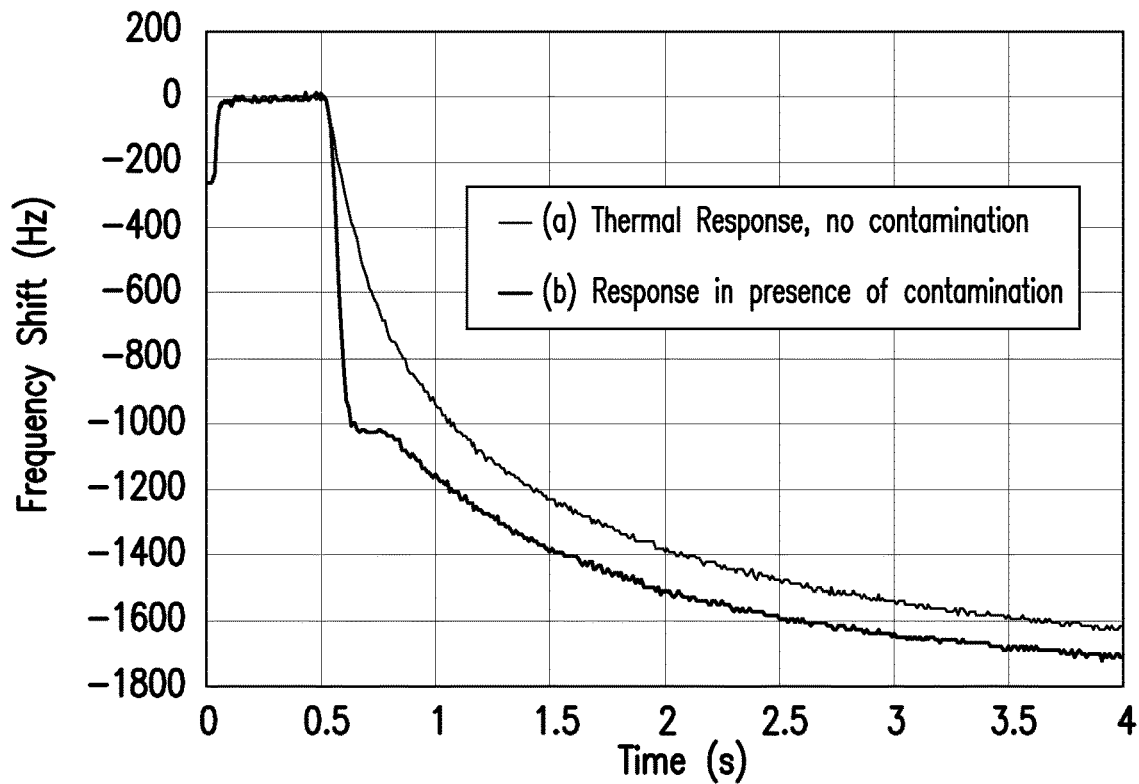
FIG. 8 shows determining the response spectra for deicing fluid, using an embodiment of an air craft air contaminant analyzer.

The frequency shift versus time is first determined in the absence of contaminants (for example, using clean laboratory air during calibration or air passing through a sterilizing filter or without first passing air through the collector). For example, the resonance frequency is measured every 0.01 seconds for 4 seconds. Resonance frequency decreases starting at 0.5 s when heating power is applied to the collector. Heat transferred to the resonator decreases its resonant frequency. This is also called the "thermal response," and illustrates the response spectra in the absence of contaminants. The response spectra is also determined in the presence of the contaminant (deicing fluid), and both response spectra are shown in FIG. 8.

Figure 9:
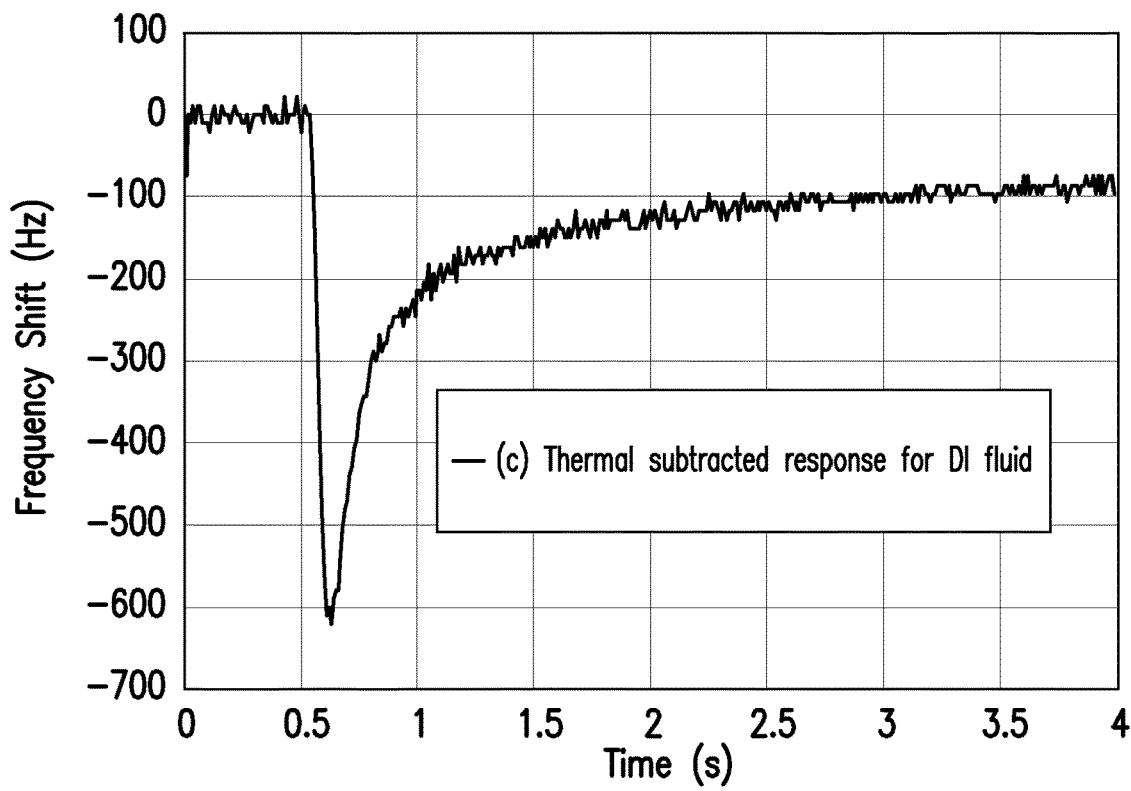
FIG. 9 shows the "thermal subtracted response" resulting from subtracting the response spectra for the absence of a contaminant (deicing fluid) from the response spectra in the presence of deicing fluid.

The first response spectra (without a contaminant) is subtracted from the second response spectra (with the contaminant), revealing the frequency shift caused by presence of the contaminant only, illustrating the "thermal subtracted response," as shown in FIG. 9.

Various features can be calculated from the "thermal subtracted responses." Four examples of such features are:

a) Maximum frequency shift (MFS): the maximum frequency shift seen during the response.

b) Sum before peak (SB): the area under the curve before the MFS.

c) Sum after peak (SA): the area under the curve after the MFS.

d) Segment #5 (S5): the average of the 37$^{th}$ thru 46$^{th}$ frequency measurements following the MFS.

Figure 10:
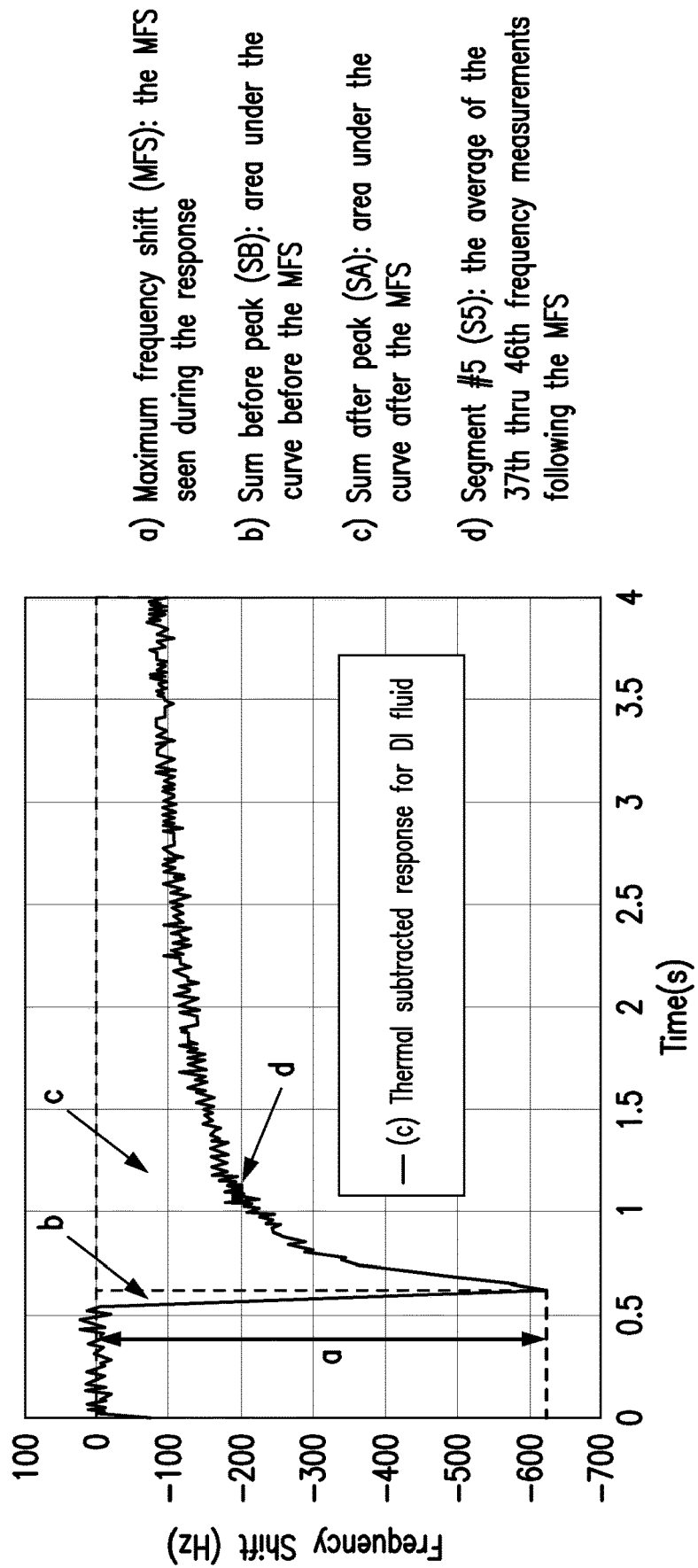
FIG. 10 shows four features that are calculated from the thermal subtracted responses: a) Maximum frequency shift (MFS); b) Sum before peak (SB); c) Sum after peak (SA); and d) Segment #5 (S5).

These four features are shown in FIG. 10.

Example 4

This example demonstrates how the feature MFS as described in Example 3 can be used by a pattern recognition algorithm to identify the contaminants.

Using an aircraft air contaminant analyzer with gravimetric sensors as described in Example 1, the frequency shift versus time is determined when the analyzer is sequentially challenged with turbine engine oil (AEROSHELL 560; Shell), hydraulic fluid (Exxon HYJET; Exxon), and deicing fluid.

Figure 11:
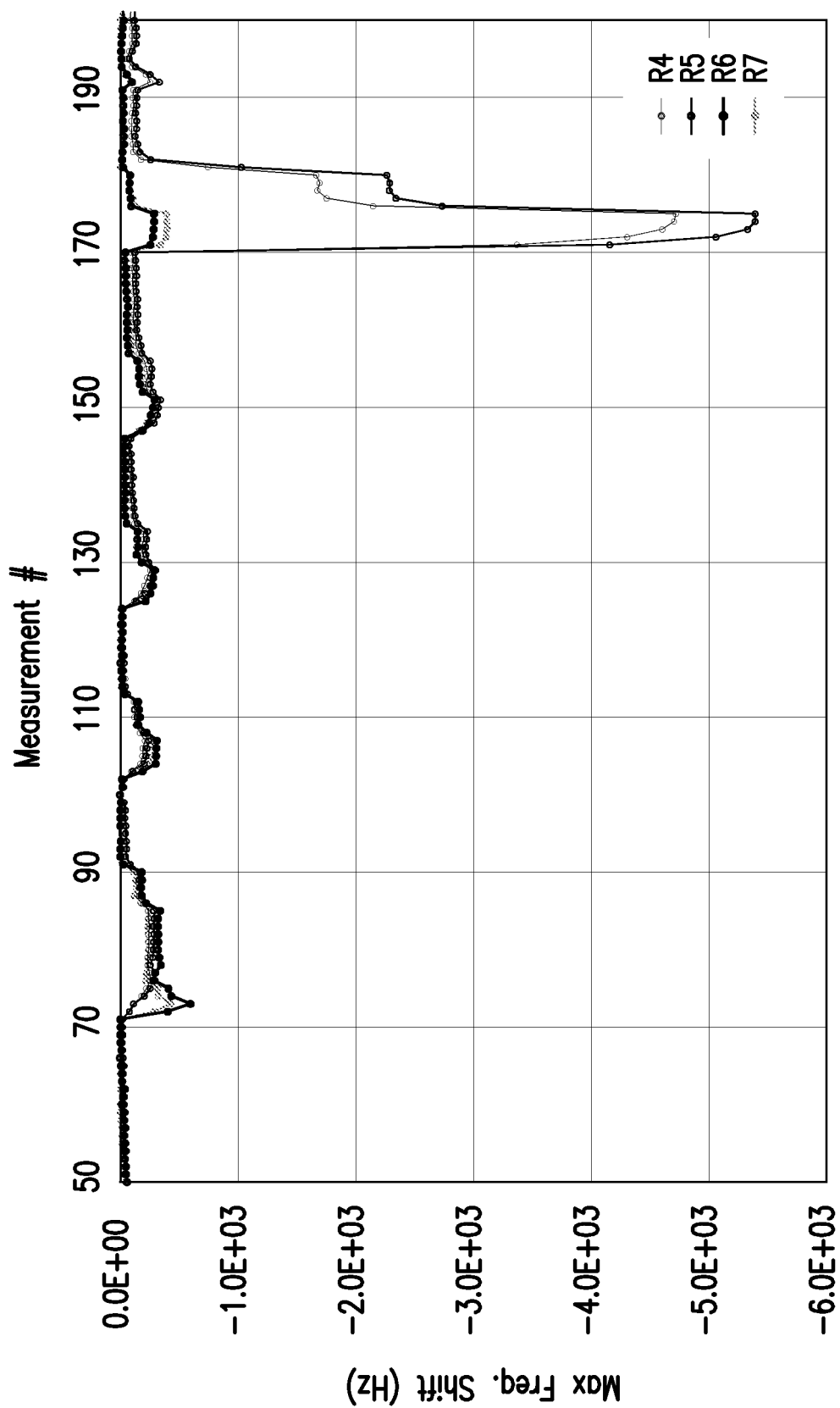
FIGS. 11 and 12 show using the feature MFS of two aircraft air contaminant collectors with different chemoselective coatings to distinguish between contaminants.

The results are shown in FIG. 11, wherein the responses (average MFSs) are similar for oil and hydraulic fluid, and different for deicing fluid.

Figure 12:
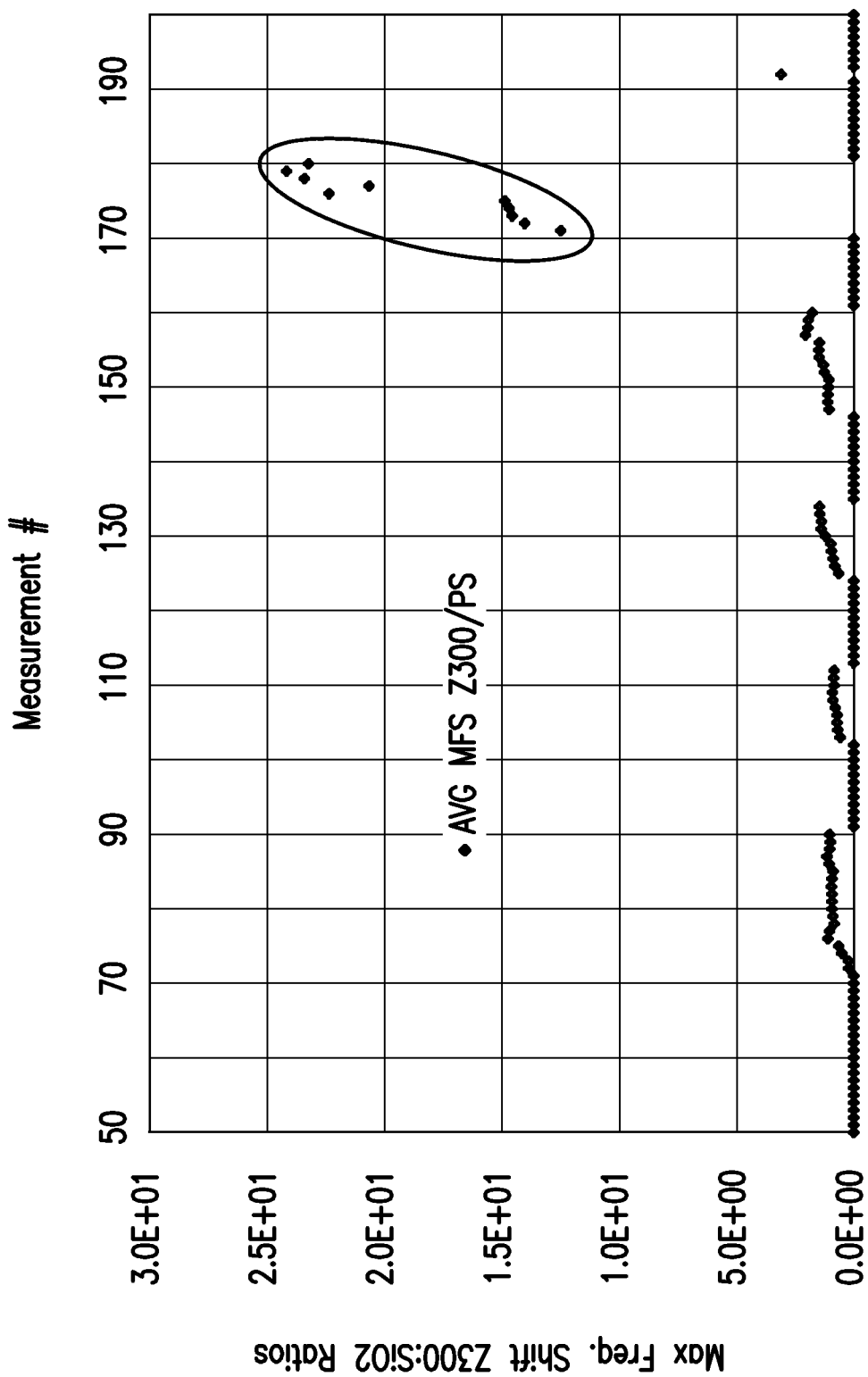

As shown in FIG. 12, the use of the feature MFS shows deicing fluid can be distinguished from hydraulic fluid and turbine engine oil: for hydraulic fluid and turbine engine oil, the ratio of the MFS feature from the gravimetric sensor next to the porous silica coated collector to the MFS feature from the gravimetric sensor next to the Z300 coated collector ranges between 0 and about 2, whereas for deicing fluid the ratio ranges between about 12 and about 23.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for determining and classifying by type aircraft air contaminants, the method comprising:

(a) passing aircraft air through an inlet of an aircraft air contaminant analyzer and through a flow-through heater block and a first valve, wherein the flow-through heater block is arranged to control temperature of the aircraft air passing through the flow-through heater block;

passing a sample of the aircraft air through the aircraft air contaminant analyzer and through at least one aircraft air contaminant collector and a second valve along a first sample flow path at a first sample flow rate and/or at a first sample flow duration, while passing another sample of aircraft air through the aircraft air contaminant analyzer and through a bypass section and a third valve along a second sample flow path bypassing the at least one aircraft air contaminant collector at a second sample flow rate and/or at a second sample flow duration,
  the at least one aircraft air contaminant collector comprising:
  (i) a microporous medium comprising microporous flow-through channels arranged across the first sample flow path, the microporous medium having a chemoselective coating; and,
  (ii) a thin film resistive heater, capable of heating to a temperature that vaporizes captured air contaminants, wherein the heater is in contact with the microporous medium;
  the aircraft air contaminant analyzer also including a gravimetric sensor arranged to generate a proportionate resonant frequency response when air contaminant mass is added to or removed from the gravimetric sensor, for classifying air contaminant type; and
  wherein the bypass section comprises a bypass channel, the bypass channel including the second sample flow path;
(a') the aircraft air contaminant analyzer further comprising:
  a pump generating flow along the first sample flow path and along the second sample flow path;
  a pressure sensor arranged between the first valve, the second valve, and the third valve; and
  a temperature sensor arranged to measure temperature in the flow-through heater block;
(b) controlling the first sample flow rate and/or the first sample flow duration through the at least one aircraft air contaminant collector along the first sample flow path while independently controlling the second sample flow rate and/or the second sample flow duration through the bypass section along the second sample flow path, wherein the first sample flow rate and/or the first sample flow duration is/are initially set at a low value for a first measurement of response signal magnitude;
(c) capturing air contaminants by the microporous medium;
(d) closing the first valve and the second valve and when a desired pressure is reached based upon a signal from the pressure sensor, closing the third valve and discontinuing passing aircraft air through the at least one aircraft air contaminant collector along the first sample flow path;
(e) heating the microporous medium to a temperature sufficient to vaporize the captured air contaminants and desorb the captured air contaminants;
(f) receiving the desorbed air contaminants on the gravimetric sensor arranged to generate a proportionate resonant frequency response when air contaminant mass is added to or removed from the gravimetric sensor;
(g) measuring the proportionate resonant frequency response generated by the gravimetric sensor as the air contaminant is added to and removed from the gravimetric sensor, determining a signal magnitude from the proportionate resonant frequency response, determining the air contaminant concentration, classifying the air contaminant type, and outputting the determined air contaminant concentration and classified air contaminant type;
(h) executing an air contaminant recognition program stored upon a computer-readable medium, including calculating air contaminant concentration using the measured signal magnitudes and first sample flow rates and the first sample flow durations along the first sample flow path;
(i) opening the first valve, the second valve, and the third valve;
(j) determining a target level for the signal magnitude, and continuously repeating (b)-(i) and measuring response signal magnitudes and adjusting the first sample flow rate and/or the first sample flow duration based upon the previously measured signal magnitude such that
  the first sample flow rate and/or the first sample flow duration is increased when the signal magnitude is lower than the target level, by an amount proportionate to how much lower the signal magnitude is below the target level, to maintain the signal magnitude at the target level, and
  the first sample flow rate and/or the first sample flow duration is decreased when signal magnitude is higher than the target level, by an amount proportionate to how much higher the signal magnitude is above the target level, to maintain the signal magnitude at the target level;
(k) executing the air contaminant recognition program stored upon the computer-readable medium, including calculating air contaminant concentration using the measured signal magnitudes and first sample flow rates and the first sample flow durations along the first sample flow path; and,
(l) outputting the determined air contaminant concentration and air contaminant type.

2. The method of claim 1, wherein (d) includes stopping operation of the pump.

3. The method of claim 1, wherein the air contaminants comprise aerosols.

4. The method of claim 1, wherein the air contaminants comprise particulates.

5. The method of claim 1, wherein the air contaminants comprise gases.

6. The method of claim 1, wherein the thin film resistive heater is capable of heating to a temperature that vaporizes captured air contaminants comprising any one or more of the following: turbine engine oil, hydraulic fluid and deicing fluid, wherein the heater is in contact with the microporous medium; and
  (c) includes capturing air contaminants comprising any one or more of the following: turbine engine oil, hydraulic fluid and deicing fluid by the microporous medium.

7. A method for determining and classifying by type aircraft air contaminants, the method comprising:
  (a) passing aircraft air through an inlet of an aircraft air contaminant analyzer and through a flow-through heater block and a first valve, wherein the flow-through heater block is arranged to control temperature of the aircraft air passing through the flow-through heater block;
  (a') the aircraft air contaminant analyzer comprising:
    at least a first aircraft air contaminant collector and a second aircraft air contaminant collector;

a first sample flow path including a first sample portion flow path and a second sample portion flow path;

wherein the first aircraft air contaminant collector is arranged along the first sample portion flow path, the aircraft air contaminant analyzer including a first adjustable flow controller communicating with the first sample portion flow path;

and the second aircraft air contaminant collector is arranged along the second sample portion flow path, the aircraft air contaminant analyzer including a second adjustable flow controller communicating with the second sample portion flow path;

wherein the aircraft air contaminant analyzer includes a second valve arranged downstream of the first sample portion flow path and the second sample portion flow path;

and, a bypass section providing a bypass sample flow path bypassing the first aircraft air contaminant collector and the first sample portion flow path, and bypassing the second aircraft air contaminant collector and the second sample portion flow path, the bypass section comprising a bypass channel, the bypass channel including the bypass sample flow path;

wherein the aircraft air contaminant analyzer includes a third valve arranged downstream of the bypass sample flow path;

the first aircraft air contaminant collector and the second aircraft air contaminant collector each separately comprising:

(i) a microporous medium comprising microporous flow through channels arranged across the sample portion flow path, the microporous medium having a chemoselective coating; and, (ii) a thin film resistive heater, capable of heating to a temperature that vaporizes captured air contaminants, wherein the heater is in contact with the microporous medium;

the aircraft air contaminant analyzer also including a gravimetric sensor near each of the first aircraft air contaminant collector and the second aircraft air contaminant collector, each gravimetric sensor arranged to generate a proportionate resonant frequency response when air contaminant mass is added to or removed from the gravimetric sensor, for classifying air contaminant type;

(a'') the aircraft air contaminant analyzer further comprising:

a pump generating flow along the first sample portion flow path, the second sample portion flow path, and along the bypass sample flow path;

a pressure sensor arranged between the first valve, the second valve, and the third valve; and a temperature sensor arranged to measure temperature in the flow through heater block;

(b) passing a first sample of the aircraft air through the aircraft air contaminant analyzer and through the first and second aircraft air contaminant collectors and the second valve along the first sample flow path at a first sample flow rate and at a first sample flow duration, including passing a first sample portion of the first sample through the first aircraft air contaminant collector and passing a second sample portion of the first sample through the second aircraft air contaminant collector;

passing the first sample portion of the aircraft air along the first sample portion flow path at a first sample portion flow rate and at a first sample portion flow duration, and passing the second sample portion of the aircraft air along the second sample portion flow path at a second sample portion flow rate and at a second sample portion flow duration, wherein the first sample portion flow duration equals the second sample portion flow duration;

while passing another sample of aircraft air through the aircraft air contaminant analyzer and through the bypass section and a third valve along the bypass sample flow path bypassing the first and second aircraft air contaminant collectors at a bypass sample flow rate and at a bypass sample flow duration;

(b') adjusting the first sample portion flow rate and the second sample portion flow rate such that the first sample portion flow rate is decreased by adjusting the first adjustable flow controller when a measured signal magnitude by the gravimetric sensor near the first aircraft contaminant collector is higher than a measured signal magnitude by the gravimetric sensor near the second aircraft contaminant collector; and the second sample portion flow rate is decreased by adjusting the second adjustable flow controller when a measured signal magnitude by the gravimetric sensor near the second aircraft contaminant collector is higher than a measured signal magnitude by the gravimetric sensor near the first aircraft contaminant collector;

(c) controlling the first sample flow rate and/or the first sample flow duration along the first sample portion flow path;

while independently controlling the bypass sample flow rate and/or the bypass sample flow duration through the bypass section along the bypass sample flow path;

wherein the first sample flow rate and/or the first sample flow duration are initially set at a low value for initial measurements of response signal magnitudes;

(d) capturing air contaminants by each microporous medium;

(e) closing the first valve and the second valve and when a desired pressure is reached based upon a signal from the pressure sensor, closing the third valve and discontinuing passing aircraft air through the first and second aircraft air contaminant collector along the first sample portion flow path and the second sample portion flow path;

(f) heating each microporous medium to a temperature sufficient to vaporize the captured air contaminants and desorb the captured air contaminants;

(g) receiving the desorbed air contaminants on each gravimetric sensor arranged to generate a proportionate resonant frequency response when air contaminant mass is added to or removed from the gravimetric sensor;

(h) measuring proportionate resonant frequency response generated by each gravimetric sensor as the air contaminant is added to and removed from each gravimetric sensor, determining the signal magnitude from the proportionate resonant frequency response, determining the air contaminant concentration, classifying the air contaminant type, and outputting the determined air contaminant concentrations and classified air contaminant types;
(i) executing an air contaminant recognition program stored upon a computer readable medium, including calculating air contaminant concentrations using the measured signal magnitudes and the first sample flow rates and the first sample flow duration along the first sample flow path;
(j) opening the first valve, the second valve, and the third valve;
(k) determining a target level for the signal magnitude, and continuously repeating (d)-(j) and measuring response signal magnitudes and adjusting the first sample portion flow rate and/or the first sample portion flow duration such that
the first sample portion flow rate and/or the first sample portion flow duration is increased when the signal magnitude of either
(iv) an average of the previously measured signal magnitudes by the gravimetric sensors near the first aircraft contaminant collector and near second aircraft contaminant collector; or
(v) the previously measured signal magnitude by the gravimetric sensor near the first aircraft contaminant collector; or
(vi) the previously measured signal magnitude by the gravimetric sensor near the second aircraft contaminant collector is lower than a target level, by an amount proportionate to how much lower the measured signal magnitude is below the target level, to maintain the signal magnitude at the target level, and
the first sample flow rate and/or the first sample flow duration is decreased when the measured signal magnitude of either
(vii) the average of the previously measured signal magnitudes by the gravimetric sensors near the first aircraft contaminant collector and near the second aircraft contaminant collector; or
(viii) the previously measured signal magnitude by the gravimetric sensor near the first aircraft contaminant collector; or
(ix) the previously measured signal magnitude by the gravimetric sensor near the second aircraft contaminant collector
is higher than the target level, by an amount proportionate to how much higher the signal magnitude is above the target level, to maintain the signal magnitude at the target level.

8. The method of claim 7, wherein (e) includes stopping operation of the pump.

9. The method of claim 7, wherein the air contaminants comprise aerosols.

10. The method of claim 7, wherein the air contaminants comprise particulates.

11. The method of claim 7, wherein the air contaminants comprise gases.

12. The method of claim 7, wherein the thin film resistive heater is capable of heating to a temperature that vaporizes captured air contaminants comprising any one or more of the following: turbine engine oil, hydraulic fluid and deicing fluid, wherein the heater is in contact with the microporous medium; and
(d) includes capturing air contaminants comprising any one or more of the following: turbine engine oil, hydraulic fluid and deicing fluid by each microporous medium.

13. A method for determining and classifying by type aircraft air contaminants, the method comprising:
(a) passing aircraft air through an inlet of an aircraft air contaminant analyzer and through a flow-through heater block and a first valve, wherein the flow-through heater block is arranged to control temperature of the aircraft air passing through the flow-through heater block;
passing a sample of the aircraft air through the aircraft air contaminant analyzer and through at least one aircraft air contaminant collector and a second valve along a first sample flow path at a first sample flow rate and/or at a first sample flow duration, while passing another sample of aircraft air through the aircraft air contaminant analyzer and through a bypass section and a third valve along a second sample flow path bypassing the at least one aircraft air contaminant collector at a second sample flow rate and/or at a second sample flow duration,
the at least one aircraft air contaminant collector comprising:
(i) a microporous medium comprising microporous flow-through channels arranged across the first sample flow path, the microporous medium having a chemoselective coating; and,
(ii) a thin film resistive heater, capable of heating to a temperature that vaporizes captured air contaminants, wherein the heater is in contact with the microporous medium;
the aircraft air contaminant analyzer also including a gravimetric sensor arranged to generate a proportionate resonant frequency response when air contaminant mass is added to or removed from the gravimetric sensor, for classifying air contaminant type; and
wherein the bypass section comprises a bypass channel, the bypass channel including the second sample flow path;
(a') the aircraft air contaminant analyzer further comprising:
a pump generating flow along the first sample flow path and along the second sample flow path;
a pressure sensor arranged between the first valve, the second valve, and the third valve; and
a temperature sensor arranged to measure temperature in the flow-through heater block;
(b) controlling the first sample flow rate and/or the first sample flow duration through the at least one aircraft air contaminant collector along the first sample flow path while independently controlling the second sample flow rate and/or the second sample flow duration through the bypass section along the second sample flow path, wherein the first sample flow rate and/or the first sample flow duration is/are initially set at a low value for a first measurement of response signal magnitude;
(c) capturing air contaminants by the microporous medium;
(d) closing the first valve and the second valve and when a desired pressure is reached based upon a signal from the pressure sensor, closing the third valve and discontinuing passing aircraft air through the at least one aircraft air contaminant collector along the first sample flow path;
(e) heating the microporous medium to a temperature sufficient to vaporize the captured air contaminants and desorb the captured air contaminants;

(f) receiving the desorbed air contaminants on the gravimetric sensor arranged to generate a proportionate resonant frequency response when air contaminant mass is added to or removed from the gravimetric sensor;

(g) measuring the proportionate resonant frequency response generated by the gravimetric sensor as the air contaminant is added to and removed from the gravimetric sensor, determining signal magnitude from the proportionate resonant frequency response, determining the air contaminant concentration, classifying the air contaminant type, and outputting the determined air contaminant concentration and classified air contaminant type;

(h) executing an air contaminant recognition program stored upon a computer-readable medium, including calculating air contaminant concentration using the measured signal magnitudes and first sample flow rates and the first sample flow durations along the first sample flow path;

(i) opening the first valve, the second valve, and the third valve;

(j) determining an upper threshold and a lower threshold for the signal magnitude for the contaminant type, and continuously repeating (b)-(i) and measuring response signal magnitudes and adjusting the first sample flow rate and/or the first sample flow duration based upon the previously measured signal magnitude such that the first sample flow rate and/or the first sample flow duration is increased when the signal magnitude is lower than the lower threshold, to a next pre-determined higher sensitivity level, to maintain the signal magnitude between the upper threshold and the lower threshold, and the first sample flow rate and/or the first sample flow duration is decreased when signal magnitude is higher than the upper threshold, to a next pre-determined lower sensitivity level, to maintain the signal magnitude between the upper threshold and the lower threshold;

(k) executing the air contaminant recognition program stored upon the computer-readable medium, including calculating air contaminant concentration using the measured signal magnitudes and first sample flow rates and the first sample flow durations along the first sample flow path; and, (l) outputting the determined air contaminant concentration and air contaminant type.

14. The method of claim 13, wherein (d) includes stopping operation of the pump.

15. The method of claim 13, wherein the air contaminants comprise aerosols.

16. The method of claim 13, wherein the air contaminants comprise particulates.

17. The method of claim 13, wherein the thin film resistive heater is capable of heating to a temperature that vaporizes captured air contaminants comprising any one or more of the following: turbine engine oil, hydraulic fluid and deicing fluid, wherein the heater is in contact with the microporous medium; and (c) includes capturing air contaminants comprising any one or more of the following: turbine engine oil, hydraulic fluid and deicing fluid by the microporous medium.

18. A method for determining and classifying by type aircraft air contaminants, the method comprising:

(a) passing aircraft air through an inlet of an aircraft air contaminant analyzer and through a flow-through heater block and a first valve, wherein the flow-through heater block is arranged to control temperature of the aircraft air passing through the flow-through heater block;

(a') the aircraft air contaminant analyzer comprising:

at least a first aircraft air contaminant collector and a second aircraft air contaminant collector;

a first sample flow path including a first sample portion flow path and a second sample portion flow path;

wherein the first aircraft air contaminant collector is arranged along the first sample portion flow path, the aircraft air contaminant analyzer including a first adjustable flow controller communicating with the first sample portion flow path;

and the second aircraft air contaminant collector is arranged along the second sample portion flow path, the aircraft air contaminant analyzer including a second adjustable flow controller communicating with the second sample portion flow path;

wherein the aircraft air contaminant analyzer includes a second valve arranged downstream of the first sample portion flow path and the second sample portion flow path;

and, a bypass section providing a bypass sample flow path bypassing the first aircraft air contaminant collector and the first sample portion flow path, and bypassing the second aircraft air contaminant collector and the second sample portion flow path, the bypass section comprising a bypass channel, the bypass channel including the bypass sample flow path;

wherein the aircraft air contaminant analyzer includes a third valve arranged downstream of the bypass sample flow path;

the first aircraft air contaminant collector and the second aircraft air contaminant collector each separately comprising:

(i) a microporous medium comprising microporous flow through channels arranged across the sample portion flow path, the microporous medium having a chemoselective coating; and, (ii) a thin film resistive heater, capable of heating to a temperature that vaporizes captured air contaminants, wherein the heater is in contact with the microporous medium;

the aircraft air contaminant analyzer also including a gravimetric sensor arranged near each respective microporous medium to generate a proportionate resonant frequency response when air contaminant mass is added to or removed from each gravimetric sensor, for classifying air contaminant type;

(a″) the aircraft air contaminant analyzer further comprising:

a pump generating flow along the first sample portion flow path, the second sample portion flow path, and along the bypass sample flow path;

a pressure sensor arranged between the first valve, the second valve, and the third valve; and a temperature sensor arranged to measure temperature in the flow through heater block;

(b) passing a first sample of the aircraft air through the aircraft air contaminant analyzer and through the first and second aircraft air contaminant collectors and the second valve along the first sample flow path at a first sample flow rate and at a first sample flow duration, including passing a first sample portion of the first sample through the first aircraft air contaminant collector and passing a second sample portion of the first sample through the second aircraft air contaminant collector;

passing the first sample portion of the aircraft air along the first sample portion flow path at a first sample portion flow rate and at a first sample portion flow duration, and passing the second sample portion of the aircraft air along the second sample portion flow path at a second sample portion flow rate and at a second sample portion flow duration, wherein the first sample portion flow duration equals the second sample portion flow duration;

while passing another sample of aircraft air through the aircraft air contaminant analyzer and through the bypass section and a third valve along the bypass sample flow path bypassing the first and second aircraft air contaminant collectors at a bypass sample flow rate and at a bypass sample flow duration;

(b') adjusting the first sample portion flow rate and the second sample portion flow rate
such that
the first sample portion flow rate is decreased by adjusting the first adjustable flow controller when a measured signal magnitude of the first aircraft contaminant collector is higher than a measured signal magnitude of the second aircraft contaminant collector; and the second sample portion flow rate is decreased by adjusting the second adjustable flow controller when a measured signal magnitude of the second aircraft contaminant collector is higher than a measured signal magnitude of the first aircraft contaminant collector;

(c) controlling the first sample flow rate and/or the first sample flow duration along the first sample portion flow path;
while independently controlling the bypass sample flow rate and/or the bypass sample flow duration through the bypass section along the bypass sample flow path;
wherein the first sample flow rate and/or the first sample flow duration are initially set at a low value for initial measurements of response signal magnitudes;

(d) capturing air contaminants by each microporous medium;

(e) closing the first valve and the second valve and when a desired pressure is reached based upon a signal from the pressure sensor, closing the third valve and discontinuing passing aircraft air through the first and second aircraft air contaminant collector along the first sample portion flow path and the second sample portion flow path;

(f) heating each microporous medium to a temperature sufficient to vaporize the captured air contaminants and desorb the captured air contaminants;

(g) receiving the desorbed air contaminants on each gravimetric sensor arranged to generate a proportionate resonant frequency response when air contaminant mass is added to or removed from the gravimetric sensor;

(h) measuring the proportionate resonant frequency response generated by each gravimetric sensor as the air contaminant is added to and removed from each gravimetric sensor, determining signal magnitude from the proportionate resonant frequency response, determining the air contaminant concentration, classifying the air contaminant type, and outputting the determined air contaminant concentrations and classified air contaminant types;

(i) executing an air contaminant recognition program stored upon a computer readable medium, including calculating air contaminant concentrations using the measured signal magnitudes and the first sample flow rates and the first sample portion flow duration along the first sample flow path;

(j) opening the first valve, the second valve, and the third valve;

(k) determining an upper threshold and a lower threshold for the signal magnitude for the contaminant type, and continuously repeating (d)-(j) and measuring response signal magnitudes and adjusting the first sample portion flow rate and/or the first sample portion flow duration such that
the first sample flow rate and/or the first sample flow duration is increased when the signal magnitude of either
(iv) an average of the previously measured signal magnitudes by the gravimetric sensors near the first aircraft contaminant collector and near the second aircraft contaminant collector; or
(v) the previously measured signal magnitude by the gravimetric sensor near first aircraft contaminant collector; or
(vi) the previously measured signal magnitude by the gravimetric sensor near the second aircraft contaminant collector
is lower than the lower threshold, to a next pre-determined higher sensitivity level, to maintain the signal magnitude at between the lower threshold and the upper threshold; and
the first sample portion flow rate and/or the first sample portion flow duration is decreased when the measured signal magnitude of either
(vii) the average of the previously measured signal magnitudes by the gravimetric sensors near the first aircraft contaminant collector and near the second aircraft contaminant collector; or
(viii) the previously measured signal magnitude by the gravimetric sensor near first aircraft contaminant collector; or
(ix) the previously measured signal magnitude by the gravimetric sensor near the second aircraft contaminant collector
is higher than the upper threshold, to a next predetermined lower sensitivity level, to maintain the signal magnitude to maintain the signal magnitude between the upper threshold and the lower threshold.

19. The method of claim 18, wherein (e) includes stopping operation of the pump.

20. The method of claim 18, wherein the air contaminants comprise aerosols.

21. The method of claim 18, wherein the air contaminants comprise particulates.

22. The method of claim 18, wherein the thin film resistive heater is capable of heating to a temperature that vaporizes captured air contaminants comprising any one or more of the following: turbine engine oil, hydraulic fluid and deicing fluid, wherein the heater is in contact with the microporous medium; and (d) includes capturing air contaminants comprising any one or more of the following: turbine engine oil, hydraulic fluid and deicing fluid by each microporous medium.

23. An aircraft air contaminant analyzer comprising:
(a) at least one aircraft air contaminant collector comprising:
   (i) a microporous medium comprising microporous flow-through channels and a chemoselective coating, wherein the microporous medium remains functional and desorbs captured air contaminants while being heated for a controlled time period, the at least one aircraft contaminant collector providing a first sample flow path, wherein the microporous medium is arranged across the first sample flow path;
   (ii) a thin film resistive heater, capable of heating to a temperature that vaporizes captured air contaminants, wherein the heater is in contact with the microporous medium;
(b) a bypass section, comprising a bypass channel, the bypass channel including a second sample flow path, the bypass channel bypassing the at least one aircraft air contaminant collector;
(c) a first substrate, having a top surface and a bottom surface; wherein the at least one contaminant collector is associated with the first substrate, the microporous medium and heater being thermally insulated from the first substrate;
(d) a gravimetric sensor arranged to generate a proportionate resonant frequency response when air contaminant mass is added to or removed from the gravimetric sensor, for classifying air contaminant type;
(e) a second substrate, having a top surface and a bottom surface; wherein the gravimetric sensor is associated with the top surface of the second substrate, the gravimetric sensor being separated from the contaminant collector by a constant distance, the gravimetric sensor being arranged to receive air contaminants desorbed from the microporous medium when the air contaminants desorbed from the microporous medium is heated;
(f) a support comprising a top surface and a bottom surface, the support comprising a common inlet port passing through the top surface and the bottom surface of the support, wherein the bottom surface of the second substrate is associated with the top surface of the support;
(g) the aircraft air contaminant analyzer further comprising:
   an aircraft air contaminant inlet port; a flow-through heater block; and a first valve, arranged upstream of the common inlet port;
   a second valve, downstream of the at least one aircraft air contaminant collector, and arranged along the first sample flow path;
   a third valve arranged along the second sample flow path;
   a pump arranged to generate flow along the first sample flow path and along the second sample flow path;
   a pressure sensor arranged between the first valve, the second valve, and the third valve; and
   a temperature sensor arranged to measure temperature in the flow-through heater block;
(h) a resonant frequency measurement device, arranged to measure the proportionate resonant frequency response generated by the gravimetric sensor as the air contaminant is added to and removed from the gravimetric sensor;
(i) a computer readable medium bearing an air contaminant recognition program and calibration data; and,
(j) a processor configured:
   to execute the air contaminant recognition program, the contaminant recognition program including a module configured to classify the air contaminant by type, and to measure response signal magnitudes from the proportionate resonant frequency response generated by the gravimetric sensor, and a module programmed to use the calibration data for comparison with the signal magnitude to calculate air contaminant concentration; and,
   to execute a sensitivity control program, the sensitivity control program including a module configured to maintain the signal magnitude at a predetermined target level or within a predetermined upper threshold and a predetermined lower threshold, by controlling the first valve, the second valve, and/or the third valve and/or the pump to:
      increase first sample flow rates and/or first sample flow durations when the signal magnitude is less than the predetermined target level or the predetermined lower threshold;
      decrease the first sample flow rates and/or the first sample flow durations when the proportionate resonant frequency response is greater than the predetermined target level or the predetermined upper threshold.

24. The aircraft air contaminant analyzer of claim 23, further comprising an additional aircraft air contaminant collector such that the analyzer comprises:
   a first aircraft air contaminant collector and a second aircraft air contaminant collector;
   the first sample flow path including a first sample portion flow path and a second sample portion flow path;
   wherein the first aircraft air contaminant collector is arranged along the first sample portion flow path, the aircraft air contaminant analyzer including a first adjustable flow controller communicating with the first sample portion flow path;
   and
   the second aircraft air contaminant collector is arranged along the second sample portion flow path, the aircraft air contaminant analyzer including a second adjustable flow controller communicating with the second sample portion flow path;
   wherein the aircraft air contaminant analyzer includes the second valve arranged downstream of the first sample portion flow path and the second sample portion flow path
   and,
   wherein the bypass section providing the second sample flow path bypasses the first aircraft air contaminant collector and the first sample portion flow path, and bypasses the second aircraft air contaminant collector and the second sample portion flow path and wherein the third valve is arranged downstream of the second sample flow path;
   the first aircraft air contaminant collector and the second aircraft air contaminant collector each separately comprising:

(i) a microporous medium comprising microporous flow through channels arranged across the sample portion flow path, the microporous medium having a chemoselective coating; and, (ii) a thin film resistive heater, capable of heating to a temperature that vaporizes captured air contaminants, wherein the heater is in contact with the microporous medium;

the aircraft air contaminant analyzer also including a gravimetric sensor arranged near each respective aircraft air contaminant collector to generate a proportionate resonant frequency response when air contaminant mass is added to or removed from the respective gravimetric sensor, for classifying air contaminant type;

the pump generating flow along the first sample portion flow path, the second sample portion flow path, and along the second sample flow path;

wherein the air contaminant recognition program includes a module configured to measure response signal magnitudes from the proportionate resonant frequency responses generated by the gravimetric sensors near each respective collector, and a module to calculate air contaminant concentrations using one or both signal magnitudes, wherein the sensitivity control program includes a module configured to maintain either an average of the previously measured signal magnitudes by the gravimetric sensors near the first aircraft contaminant collector and near the second aircraft contaminant collector; or the previously measured signal magnitude of the gravimetric sensor near the first aircraft contaminant collector; or the previously measured signal magnitude of the gravimetric sensor near the second aircraft contaminant collector;

at a predetermined target level or within a predetermined upper threshold and a predetermined lower threshold, by controlling the first valve, the second valve, and/or the third valve and/or the pump to:

increase the first sample flow rates and/or the first sample flow durations when the signal magnitude is less than the predetermined target level or the predetermined lower threshold;

decrease the first sample flow rates and/or the first sample flow durations when the signal magnitude is greater than the predetermined target level or the predetermined upper threshold.

25. The aircraft air contaminant analyzer of claim 24, wherein the first aircraft air contaminant collector and the second aircraft air contaminant collector each comprise a thin film resistive heater capable of heating to a temperature that vaporizes captured air contaminants comprising any one or more of the following: turbine engine oil, hydraulic fluid and deicing fluid, wherein the heater is in contact with the microporous medium.

26. The aircraft air contaminant analyzer of claim 23, wherein the thin film resistive heater is capable of heating to a temperature that vaporizes captured air contaminants comprising any one or more of the following: turbine engine oil, hydraulic fluid and deicing fluid, wherein the heater is in contact with the microporous medium.

* * * * *